US005827666A

United States Patent [19]
Finn et al.

[11] Patent Number: 5,827,666
[45] Date of Patent: Oct. 27, 1998

[54] SYNTHETIC MULTIPLE TANDEM REPEAT MUCIN AND MUCIN-LIKE PEPTIDES, AND USES THEREOF

[75] Inventors: Olivera J. Finn, Pittsburgh, Pa.; J. Darrell Fontenot, Espanola, N. Mex.; Ronald C. Montelaro, Wexford, Pa.

[73] Assignee: University of Pittsburgh, Pittsburgh, Pa.

[21] Appl. No.: 288,059

[22] Filed: Aug. 10, 1994

Related U.S. Application Data

[63] Continuation-in-part of Ser. No. 99,354, Jul. 30, 1993.
[51] Int. Cl.$^6$ .................. G01N 33/53; G01N 33/574; C07K 1/00; C07K 14/00
[52] U.S. Cl. .................... 435/7.1; 435/7.23; 435/7.6; 435/7.9; 530/350
[58] Field of Search .................... 435/7.1, 7.23, 435/7.6, 7.9; 530/350

[56] References Cited

FOREIGN PATENT DOCUMENTS 0369816  5/1990  European Pat. Off. ........ C12P 21/08

OTHER PUBLICATIONS

Gendler et al, 1988, "A Highly Immunogenic Region . . . " J. Biol. Chem. 263(26):12820–12823.
Bara, et al, 1993, "A Fucose Residue can Mask . . . " International J. Cancer 54:607–613.
von Mensdorff–Pouilly et al., "Cancer Vaccines, 1996–Oct. 7–9, 1996, N.Y. Humoral Immune Response to Polymeric Epithelial Mucin . . . Tumors".
Petrarca, et al. –"Human Anti–Pem (Polymorphic Epithelial Mucin) Antibodies Production by B Lymphocytes Selected From . . . Nodes".
McGuckin, et al.–"Antibodies Reactive with the MUC1 VNTR are Present in Ovarian Cancer Patients and Healthy Women".
Carol Clayberger et al., Peptides Corresponding to the CD8 and CD4 Binding Domains of HLA Molecules Block T Lymphocyte Immune Responses In Vitro[1], pp. 946–951.
Alessandro Sette et al., Peptide Binding To The Most Frequent HLA–A Class I Alleles Measured By Quantitative Molecular Binding Assays, pp. 813–822.
Niklas Ahlborg et al., "B– and T–cell responses in congenic mice to repeat sequences of the malaria antigen Pf332: effects of the number of repeats", Imunology Letters, 40 (1994) 147–155.
Michael N. Starnbach et al., Cells Infected with Yersinia Present an Epitope to Class I MHC–Restricted CTL[1], The Journal of Immunology, pp. 1603–1612.
Thronsten Vogel et al., The Majority of Neutralizing Abs in HIV–1–Infected Patients Linear V3 Loop Sequences, (1994) The Journal of Immunology, pp. 1895–1904.

Ichiro Yoshino et al., "HER2/neu–derived Peptides Are Shared Antigens among Human Non–Small Cell Lung Cancer and Ovarian Cancer", Cancer Research 54 3387–3390, Jul. 1, 1994.
Jean–Pierre Cabaniols et al., "Dose–dependent T cell tolerance to an immunodominant self peptide", Eur. J. Immunol. 1994 24: 1743–1749.
Gilles Benichou et al., "Limited T Cell Response to Donor MHC Peptides During Allograft Rejection", The Journal of Immunology, pp. 938–945.
Isao Nishimori et al., "Influence of Acceptor Substrate Primary . . . N–Acetylgalactosaminyltransferase", The Journal of Biological Chemistry, Vo. 269, No. 23, Jun. 10, pp. 16123–16130, 1994.
Hareuveni et al., "Vaccination against tumor cells expressing breast cancer epithelial tumor antigen", Proc. Natl. Acad. Sci. USA, vol. 87, pp. 9498–9502, Dec. 1990, Medical Sciences.
Acres et al., "Vaccinia Virus MUC1 . . . Antigen", Journal of Immunotherapy, 14:136–143, 1993.
Ding et al., "Immunogenicity of synthetic peptides . . . MUC1 gene", Cancer Immunol Immunother (1993), 36: 9–17.
Abstract – "Mucin Based Immunity and Immunotheraphy of Cancer", by O.J. Finn, Dept. of Molecular Genetics and Biochemisty, University of Pittsburgh School of Medicine, Pittsburgh, PA 15261, USA.
J. Darrell Fontenot, et al., Biophysical Characterization of One–, Two–, and Three–Tandem Repeats of Human Mucin (muc–1) Protein Core[1], Cancer Research 53, 5386–5394, Nov. 15, 1993.
J. D. Fontenot, et al., Synthesis of Large Multideterminant Peptide Immunogens Using A poly–Proline β–Turn Helix Motiff, Peptide Research, 330–336, vol. 6, No. (1993).
Yasuo Kotera, et al., Humoral Immunity against a Tandem Repeat Epitope of Human Mucin MUC–1 in Sera From Breast, Pancreatic, and Colon Cancer Patients[1], Advances in Brief, Cancer Research 54, 2856–2860, Jun. 1, 1994.
Olivera J. Finn, Antigen–specific, MHC–unrestricted T cells, Biotherapy 4: 239–249, 1992, Dept. of Molecular Genetics and Biochemisty, University of Pittsburg School of Medicine, Pittsburgh, PA 15261, USA.

Primary Examiner—Lynette F. Smith
Attorney, Agent, or Firm—Cushman Darby & Cushman IP Group of Pillsbury Madison & Sutro, LLP

[57] ABSTRACT

The present invention relates to novel synthetic muc-1 peptides and muc-1-like analogs including at least two 20-amino acid tandem repeats of muc-1, which synthetic muc-1 and muc-1-like peptides are capable of attaining native conformation in the absence of glycosylation. The invention also relates to methods of producing the peptides. The invention further relates to uses of the peptides, such as for vaccines and diagnostic testing.

8 Claims, 14 Drawing Sheets

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Pro Asp Thr Arg Pro Ala Pro Gly Ser Thr Ala Pro Pro Ala His Gly
1               5                   10                  15
Val Thr Ser Ala
            20

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Pro Thr Thr Thr Pro Ile Thr Thr Thr Thr Thr Val Thr Pro Thr Pro
1               5                   10                  15
Thr Pro Thr Pro Thr Gly Thr Thr Gln Thr
            20                  25

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

His Ser Thr Pro Ser Phe Thr Ser Ser Ile Thr Thr Thr Glu Thr Thr
1               5                   10                  15
Ser ( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Thr Ser Ser Val Ser Thr Gly His Ala Thr Ser Leu Pro Val Thr Ala
1               5                   10                  15

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Pro  Lys  Leu  Lys  Leu
1                    5
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Gly  Val  Thr  Ser  Ala
1                    5
```

( 2 ) INFORMATION FOR SEQ ID NO:7:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ala  Pro  Asp  Thr  Arg  Pro  Ala  Pro  Gly  Ser  Thr  Ala  Pro  Pro  Ala  His
1                   5                        10                       15
Gly  Val  Thr  Ser  Ala  Pro  Asp  Thr  Arg  Pro  Ala  Pro  Gly  Ser  Thr  Ala
               20                       25                       30
Pro  Pro  Ala  His  Gly  Val  Thr  Ser
          35                  40
```

( 2 ) INFORMATION FOR SEQ ID NO:8:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Xaa  Pro  Xaa  Xaa  Xaa  Pro  Xaa  Pro  Gly  Ser  Thr  Ala  Pro  Pro  Ala  His
1                   5                        10                       15
Gly  Val  Thr  Ser  Ala  Pro  Xaa  Xaa  Xaa  Pro  Xaa  Pro  Gly  Ser  Thr  Ala
               20                       25                       30
Pro  Pro  Ala  His  Gly  Val  Thr  Ser
          35                  40
```

( 2 ) INFORMATION FOR SEQ ID NO:9:

( i ) SEQUENCE CHARACTERISTICS:
        ( A ) LENGTH: 19 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

Pro Asp Thr Arg Pro Ala Pro Ser Thr Ala Pro Pro Ala His Gly Val
1               5                   10                  15

Thr Ser Ala (2) INFORMATION FOR SEQ ID NO:10:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

Gly Pro Gly Arg Ala Phe Pro Ala Pro Ser Thr Ala Pro Pro Ala His
1               5                   10                  15

Gly Val Thr Ser Ala
            20

(2) INFORMATION FOR SEQ ID NO:11:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

Pro Asp Thr Arg Pro Ala Pro Ser Thr Ala Pro Pro Ala Gly Pro Gly
1               5                   10                  15

Arg Ala Phe (2) INFORMATION FOR SEQ ID NO:12:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

Pro Asp Thr Arg Pro Ala Pro Gly Ser Thr Ala Pro Pro Ala Gly His
1               5                   10                  15

Val Thr Ser Ala
            20

(2) INFORMATION FOR SEQ ID NO:13:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide ( x i ) SEQUENCE DESCRIPTION: SEQ ID NO:13:

Pro Asp Thr Arg Pro Ala Pro Gly Ser
1               5

( 2 ) INFORMATION FOR SEQ ID NO:14:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:14:

Asp Thr Arg Pro Ala Pro Gly Ser Thr
1               5

( 2 ) INFORMATION FOR SEQ ID NO:15:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:15:

Thr Arg Pro Ala Pro Gly Ser Thr Ala
1               5

( 2 ) INFORMATION FOR SEQ ID NO:16:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:16:

Ala Pro Gly Ser Thr Ala Pro Pro Ala
1               5

( 2 ) INFORMATION FOR SEQ ID NO:17:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:17:

Pro Gly Ser Thr Ala Pro Pro Ala His
1               5

( 2 ) INFORMATION FOR SEQ ID NO:18:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide (x i) SEQUENCE DESCRIPTION: SEQ ID NO:18:

Gly Ser Thr Ala Pro Pro Ala His Gly
1               5

(2) INFORMATION FOR SEQ ID NO:19:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:19:

Ser Thr Ala Pro Pro Ala His Gly Val
1               5

(2) INFORMATION FOR SEQ ID NO:20:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:20:

Thr Ala Pro Pro Ala His Gly Val Thr
1               5

(2) INFORMATION FOR SEQ ID NO:21:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:21:

Ala Pro Pro Ala His Gly Val Thr Ser
1               5

(2) INFORMATION FOR SEQ ID NO:22:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:22:

Pro Pro Ala His Gly Val Thr Ser Ala
1               5

(2) INFORMATION FOR SEQ ID NO:23:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i) MOLECULE TYPE: peptide ( x i ) SEQUENCE DESCRIPTION: SEQ ID NO:23:

Ala His Gly Val Thr Ser Ala Pro Asp
1               5

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

His Gly Val Thr Ser Ala Pro Asp Thr
1               5

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Gly Val Thr Ser Ala Pro Asp Thr Arg
1               5

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Thr Ser Ala Pro Asp Thr Arg Pro Ala
1               5

( 2 ) INFORMATION FOR SEQ ID NO:27:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

Ala Pro Asp Thr Arg Pro Ala Pro Gly
1               5

( 2 ) INFORMATION FOR SEQ ID NO:28:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

Gly Val Thr Ser Ala Pro Asp Thr Arg Pro Ala Pro Gly Ser Thr Ala
1               5                   10                  15

Pro Pro Ala His Gly Val Thr Ser Ala
            20              25

( 2 ) INFORMATION FOR SEQ ID NO:29:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:29:

Pro Asp Thr Arg Pro
1               5

( 2 ) INFORMATION FOR SEQ ID NO:30:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:30:

Thr Ala Glu Asn Ala Glu Tyr Leu Arg Val
1               5                   10

( 2 ) INFORMATION FOR SEQ ID NO:31:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:31:

Ala Pro Asp Thr Arg
1               5

( 2 ) INFORMATION FOR SEQ ID NO:32:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:32:

Pro Asp Thr Arg Pro Ala Pro Gly Ser Thr Ala Pro Pro Ala His Gly
1               5                   10                  15

Val Thr Ser Ala
            20

( 2 ) INFORMATION FOR SEQ ID NO:33:

( i ) SEQUENCE CHARACTERISTICS:
      ( A ) LENGTH: 60 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

Thr Ile Thr Pro Pro Gln Ala Met Gly Pro Asn Leu Val Leu Pro Asp
1               5                   10                  15
Gln Lys Pro Pro Ser Arg Gln Ser Gln Thr Gly Ser Lys Val Ala Thr
                20                  25                  30
Gln Arg Pro Gln Thr Asn Glu Ser Ala Pro Arg Ser Val Ala Pro Thr
            35                  40                  45
Thr Val Gly Pro Lys Arg Ile Gly Thr Gly Asp Arg
        50                  55                  60

(2) INFORMATION FOR SEQ ID NO:34:

(i) SEQUENCE CHARACTERISTICS:
    (A) LENGTH: 42 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:34:

Thr Pro Pro Gln Ala Met Gly Pro Asn Leu Val Leu Pro Asp Gln Lys
1               5                   10                  15
Pro Pro Ser Arg Gln Ser Gln Thr Gly Ser Lys Val Ala Thr Gln Arg
                20                  25                  30
Pro Gln Thr Asn Glu Ser Ala Pro Arg Ser
            35                  40

(2) INFORMATION FOR SEQ ID NO:35:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:35:

Tyr Pro His Phe Met Pro Thr Asn Leu
1               5

(2) INFORMATION FOR SEQ ID NO:36:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:36:

Tyr Pro His Ala Met Pro Thr Asn Leu Ser
1               5                   10

SYNTHETIC MULTIPLE TANDEM REPEAT MUCIN AND MUCIN-LIKE PEPTIDES, AND USES THEREOF

FIELD OF THE INVENTION

This application is a Continuation-in-part of application Ser. No. 08/099,354, filed Jul. 30, 1993, the entire contents of which are incorporated herein by reference.

The present invention relates to synthetic multiple tandem repeat peptides and methods of synthesizing the peptides. The present invention also relates to uses of the peptides, such as in vaccines and diagnostic tests for human cancers and infectious diseases using the framework structure of the tandemly repeating synthetic peptides. This invention was made with government support under CA-56103 awarded by the National Institutes of Health. The government has certain rights in the invention.

BACKGROUND INFORMATION

Mucins are large secreted and/or transmembrane glycoproteins with greater than 50% of their molecular weight derived from O-linked carbohydrate attached to serine and threonine residues (for a review see Strouss, G. J. and Dekker, Critical Reviews in Biochemistry and Molecular Biology, 27½: 57–92, 1992). The bulk of the glycosylation is contained within a domain composed of tandemly repeated sequences of 10–81 amino acids per repeat (Gum, et al., J. Biol. Chem., 264: 6480–6487, 1989, Gum, et al. Biochem. Biophys. Res. Commun. 171: 407–415, 1990, Lan, et al., J. Biol. Chem., 265: 15294–15299, 1990, Lan, et al. Cancer Res., 50: 2997–3001, 1990, and Porchet, et al., Biochem. Biophys. Res. Commun., 175: 414–422, 1991). Mucins are produced by cells of epithelial lineage and recently, expression of certain epitopes on one of the mucins, polymorphic epithelial mucin (PEM) encoded by the muc-1 gene, has been identified as being associated with tumors (Hilkens, et al., Cancer Res., 49: 786–793, 1989 and Jerome, et al., Cancer Res., 51: 2908–2915, 1991).

Studies with monoclonal antibodies reactive with epithelial tumors and corresponding normal tissues reveal that there can be different epitopes associated with mucins from malignant cells as opposed to normal cells (Jerome, et al., Cancer Res., 51: 2908–2916, 1991, Girling, et al., Int. J. Cancer, 43: 1072–1076, 1989, Taylor-Papadimitriou, J., Int. J. Cancer, 49: 1–5, 1991). This is in part due to aberrant glycosylation in certain tumors which results in the exposure of the mucin tandem repeat protein core on the cell surface (Hilkens, et al., Cancer Res., 49: 786–793, 1989, Girling, et al., Int. J. Cancer, 43: 1072–1076, 1989, Sell, Progress Path., 21: 1003–1019, 1990, Devine, et al., Cancer Res. 51: 5826–56836, 1991, and Itzkowitz, et al., Gastroenterol., 100: 1691–1700, 1991). The exposure of the protein core of certain mucins found on malignant cells, combined with the ability of the immune system to respond to these structures (Jerome, et al., Cancer Res., 51: 2908–2916, 1991 and Barnd, et al., PNAS USA, 86: 7159–7163, 1989), offers a unique opportunity to utilize mucin-based vaccines for specific immunotherapy of tumors.

The development of effective vaccine and immunotherapies for human cancers and infectious agents often is dependent on the generation of protective immune responses to specific domains of membrane proteins. Examples include: the tandem repeat (TR) domain of the breast, pancreatic, and ovarian tumor antigen, human mucin muc-1 (Barnd et al., PNAS USA, 86: 7159–7163, 1989; Jerome et al., Cancer Res., 51: 2908–2916, 1991), the principal neutralizing domain of HIV-1 (Javaherian et al., PNAS USA, 86: 6768–6772, 1989; Javaherian et al., Science, 250: 1590–1593, 1990) and the proline rich neutralization domain of the feline leukemia virus external surface unit protein (gp-70) (Nunberg et al., PNAS, 81: 3675–3679, 1984; Elder et al., J. Virol., 61: 8–15, 1987; Strouss et al., J. Virol., 61: 3410–3415, 1987; Nick et al., J. Gen. Virol., 71: 77–83, 1990).

It was recently shown that protein core of the human muc-1 TR domain (Fontenot et al., in press 1993A) and the feline leukemia virus PRN domain of gp-70 (Fontenot et al., in press 1993B) form poly-proline β-turn helixes (Matsushima et al., Function and Genetics, 7: 125–155, 1990). Some common characteristics of the poly-proline β-turn helix include: (1) Approximately 20–60% proline, and a high content of glycine, serine and glutamine: (2) Low predicted α-helix and β-sheet secondary structure content and a high predicted content of β-turns: (3) A circular dichroism spectrum consistent with high turn content and low α-helix and β-sheet secondary structure content: (4) Intrinsic viscosity values consistent with the formation of extended rod-shaped structures (Matsushima et al., 1990).

In many cases, the use of the entire glycoprotein as an immunogen for the development of effective vaccines and immunotherapies for human cancers and infectious agents has proven either ineffective due to a lack of immunogenicity, or results in the enhancement of infection and disease due to the inclusion of nonprotective epitopes (Osterhaus et al. Vaccine, 7:137–141, 1989; Gilbert et al. Virus Research, 7:49–67, 1987; Burke, D. Perspect. Biol. Med., 35:511–530, 1992).

The use of synthetic peptides as vaccines can circumvent many of the problems associated with recombinant vaccines. The advantages of the use of synthetic peptides that correspond to specific membrane protein domains include: selection and inclusion of only protective epitopes; exclusion of disease enhancing epitopes and infectious material; and, synthetic peptides antigens are chemically well defined and can be produced at a reasonable cost (Arnon and Horwitz, Curr. Opin. Immunol., 4:449–453, 1992).

The disadvantages are that small synthetic peptides may not contain the precise amino acid sequences necessary for processing and binding to major histocompatibility complex (MHC) class I and class II proteins, for presentation to the immune system (Rothbard, Biotechnology, 20:451–465, 1992). Another disadvantage is that the solution structure of small peptides may be different than that found in the native protein and therefore not induce humoral immunity of the proper specificity and affinity to provide protective immunity (Bernard et al. Aids Res. and Hum. Retroviruses, 6:243–249, 1990).

However, peptide fragments of larger proteins which are rich in proline, peptides containing b-turns, and peptides with proline rich direct sequence repeats have been shown to maintain native structure in solution and be immunogenic (Broekhuijsen et al., J. Gen. Virol., 68:3137–3145, 1987; Bhandary et al., Int. J. Peptide Protein Res. 36:122–127, 1990; Dyson et al., J. Mol. Biol., 201:201–217, 1988; Dyson et al., Biochemistry 31:1458–1463, 1992; Mayo et al., Biochemistry 30:8251–8267, 1991; Richman and Reese, Proc. Natl. Acad. Sci. U.S.A., 85:1662–1666, 1988) and seem to have potential as vaccine candidates. These include the human mucin and tumor antigen (muc-1) tandem repeat (TR) domain (Gendler et al. J. Biol. Chem., 26:12820–12823, 1988; Lan et al., Cancer Res. 50:2997–3001, 1990; Barnd et al., Proc. Natl. Acad. Sci.

U.S.A., 86:7159–7163, 1989; Jerome et al., Cancer Res., 51:2908–2916, 1991), the retroviral proline rich domains of feline leukemia virus gp70 (Donahue et al., J. Virol., 62:722–731, 1988), murine leukemia virus gp70 (Battini et al., J. Virol., 66:1468–1475, 1992), and Gibbon ape leukemia virus (Delassus et al., Virology, 53:205–213, 1989), and the tandem repeats of the H.8 lipoprotein of Neisseria gonorrhoeae (Baehr et al., Mol. Microbiol. 3:49–55).

Mucins are glycoproteins abundantly present at the luminal side of ductal epithelial cells and on tumors derived from this cell type. Numerous mucin specific antibodies have been derived following immunization of animals with normal or malignant epithelial cells. They were initially thought to recognize different molecules but were determined in most instances to react with various carbohydrate mucin epitopes. Heterogeneity of mucin molecules as defined by carbohydrate specific antibodies appeared to be extensive. Antibodies were reported which reacted with both normal and tumor mucins, some that exhibited apparent tumor specificity, some that showed organ specificity, and others that reacted with mucins from all organ sites. The most discriminating were antibodies which reacted with peptide epitopes on the mucin polypeptide core. Some of these antibodies resulted from immunizations with whole mucin or epithelial cell tumors, providing evidence that some peptide epitopes must be exposed on this highly glycosylated molecule and on the tumor cell surface (Kufe D, Inghirami M, Abe D, Hayes H, Justi-Wheeler H and Schlom J. Differential reactivity of a novel monoclonal antibody (DF3) with human malignant versus benign tumors. Hybridoma 3: 223, 1984; Hilkens J, Buijs F, Hilgers J, et al. Monoclonal antibodies against human milk-fat globule membranes detecting differentiation antigens of the mammary gland and its tumors. Int. J. Cancer 34: 197, 1984; Burchell J, Gendler S and Taylor-Papadimitriou J. Development and characterization of breast cancer reactive monoclonal antibodies directed to the core protein of the human milk mucin. Cancer res. 47: 5476, 1987; Girling A, Bartkova J, Burchell J, et al. A core protein epitope of the polymorphic epithelial mucin detected by the monoclonal antibody SM-3 is selectively exposed in a range of primary carcinomas. Int. J. Cancer 43: 1072, 1989; Xing P X, Tjandra J J, Stacker S A, et al. Monoclonal antibodies reactive with mucin expressed in breast cancer. Immunol. cell Biol. 67: 183, 1989; Gendler S J, Burchell J M, Duhig T, et al. Cloning of a partial CDNA encoding differentiation and tumor-associated mucin glycoproteins expressed by human mammary epithelium. Proc. Natl. Acad. Sci. USA 84: 6060, 1987).

The nature of mucins produced by different organs, as well as possible differences between tumor derived and normal epithelial cell-derived mucins became clear only recently, following isolation of cDNA clones for breast (Gendler S J, Lancaster C A, Taylor-Papadimitrou J, et al. Molecular cloning and expression of human tumor-associated polymorphic epithelial mucin. J. Biol. Chem. 265: 15286* 1990; Siddiqui J, Abe M, Hayes E, Shani E, Yunis E and Kufe D. Isolation and sequencing of a CDNA coding for the human DF3 breast carcinoma-associated antigen. Proc. Natl. Acad. Sci. USA 85: 2320, 1988; Ligtenberg M J L, Vos H L, Gennissen A M C and Hilkens J. Episialin, a carcinoma-associated mucin, is generated by a polymorphic gene encoding splice variants with alternative amino termini. J. Biol. Chem. 265: 5573 1990) pancreas (Gum J R, Hicks J W, Swallow D M, et al.Molecular cloning of CDNAS derived from a novel human intestinal mucin gene. Biochem. Biophys. Res. Commun. 171: 407, 1990) small intestine (Gum J R, Byrd J C, Hicks J W, Toribara N W, Lamport D T A and Kim T S. Molecular cloning of human intestinal mucin cDNAs. Sequence analysis and evidence for genetic polymorphism. J. Biol. Chem. 264: 6480, 1989; Gum J R, Hicks J W, Swallow D M, et al. Molecular cloning of CDNAS derived from a novel human intestinal mucin gene. Biochem. Biophys. Res. Commun. 171: 407, 1990) and bronchoepithelial cell mucin (Porchet N, Van Cong N, Dufosse J, et al. Molecular cloning and chromosomal localization of a novel human tracheobronchial mucin CDNA containing tandemly repeated sequences of 48 base pairs. Biochem. Biophys. Res. Commun. 175: 414, 1991). Comparison of the cDNA's indicated important similarities in the overall structure of the molecule, but also showed that at least four different genes located on different chromosomes encode mucin molecules, and that the expression of these genes is tissue specific. The sequences of all the genes cloned from breast adenocarcinomas were nearly identical, and those in turn were identical to the sequence of the gene cloned from a pancreatic adenocarcinoma. They are also found in colon carcinomas. They were named MUC 1. Two other genes isolated from a small intestine CDNA library and expressed at low levels in colon carcinomas (MUC 2 and MUC 3) are distinct from one another, and from the fourth, tracheobronchial mucin gene MUC 4.

The most unifying feature of all the mucin genes and proteins is the presence of numerous (between 40 and 100) tandem repeats which comprise approximately twothirds of the molecule. The amino acid sequence of the repeats is abundant in serines and threonines, sites of O-linked glycosylation. The amino terminus consists of a putative signal peptide followed by degenerate tandem repeats and the carboxyl terminus contains degenerate tandem repeats, a unique transmembrane sequence and cytoplasmic tail. Table A below shows the tandem repeat structure of the breast and pancreas mucin cDNA (MUC 1). It consists of 60 nucleotides encoding a polypeptide of 20 amino acids in length. Five O-linked glycosylation sites (2 serines and 3 threonines) are present per repeat.

TABLE A

Table A compares the tandem repeat animo acid sequence encoded by the four genes.
Repetitive sequences in human mucins

| Mucin | Amino Acid Residues (see SEQ ID NOS: 1–4, respectively) |
|---|---|
| MUC 1 | PDTRPAPGSTAPPAHGVTSA |
| MUC 2 | PTTTPITTTTTVTPTPTPTPTGTTQT |
| MUC 3 | HSTPSFTSSITTTETTS |
| MUC 4 | TSSVSTGHATSLPVTA |

The present invention provides methods for synthesizing long peptides having poly-proline β-turn helices, and methods for modifying these synthetic poly-proline helices for the design of new antigens by tandemly repeating important B- or T- cell epitopes or coupling B- and T- cell epitopes to produce antigens of larger sizes.

The invention is based on the novel method of synthesizing very long peptides of multiple tandem repeats having a poly-proline β-turn structural motif, such as human mucin (muc-1) peptides. The peptides of the invention attain native conformation in the absence of glycosylation, reflecting the structure seen in native mucin.

The invention also relates to methods of designing antigens which are able to induce an immune response. This aspect of the invention is based on the previously identified MHC-unrestricted T-cell reactivity against mucin seen in patients with breast and pancreatic adenocarcinomas expressing this protein (Jerome et al., Cancer Res., 51:2908–2916, 1991; Barnd et al., Proc. Natl. Acad. Sci. U.S.A., 86:7159–7163, 1989; Jerome et al., Cancer Res., 52:5985–5990, 1992) in addition to the newly discovered characteristic of the structure of the poly-repeat synthetic mucin peptide. (Fontenot et al., "Biophysical Characterization of One-, Two-, and Three-Tandem Repeats of the Human Mucin (MUC-1) Protein Core," submitted to Cancer Research.)

The poly-repeat mucin peptide allows the removal of several amino acids from the primary epitope of mucin without interfering with the structure of the tandem repeats important for native conformation and for the MHC-unrestricted T-cell reactivity. It is possible to replace the uninterfering amino acids of the mucin epitope with amino acids from epitopes of important antigens allowing an unrestricted T-cell reactivity to the newly designed immunogen.

SUMMARY OF THE INVENTION

The invention relates to a synthetic muc-1 peptide comprising at least two 20-amino acid tandem repeats of muc-1, which synthetic muc-1 peptide is capable of attaining native conformation in the absence of glycosylation. For instance, the synthetic muc-1 peptide may comprise 2, 3, 4, 5 or more tandem repeats of muc-1.

In another embodiment, the invention relates to a synthetic muc-1-like peptide that comprises at least two 20-amino acid tandem repeats of muc-1 and a foreign amino acid sequence, which peptide is capable of attaining native conformation in the absence of glycosylation. For instance, the synthetic muc-1-like peptide may comprise 2, 3, 4, 5 or more tandem repeats of muc-1. The foreign amino acid sequence may be an epitope, such as, for instance an antigenic epitope corresponding to a virus (for example, HIV), a bacteria, a parasite, or cancer (for example, pancreatic cancer, breast cancer, ovarian cancer or colon cancer). Thus, the peptide is muc-1-like, or an analog of muc-1 where a "foreign" epitope is appropriately inserted to form an immunologically native synthetic antigen.

The synthetic muc-1 and muc-1-like peptides of the present invention may be 40, 60, 80 or, preferably, 105 amino acids in length, or even larger and may be covalently linked to a pharmaceutically acceptable adjuvant.

In a further embodiment, the present invention relates to a method of producing a mucin peptide having at least two tandem repeats, which peptide is capable of attaining native conformation in the absence of glycosylation. The method relates to standard solid state synthesis protocols, with several modifications. Conventional methodology is employed with the following modifications. Synthesis is stopped when the primary sequence reaches 30 amino acids in length. One half of the resin-bound 30 amino acid peptide is then removed. A monitor step is then employed to monitor the completeness of the reaction. The reaction cycle is then continued until the desired length is obtained.

In another embodiment, the present invention relates to a method of producing muc-1-like peptides having at least two tandem repeats and a foreign amino acid sequence, which muc-1-like peptide is capable of attaining native conformation in the absence of glycosylation. The method relates to standard solid state synthesis protocols, with the several modifications mentioned hereinabove. The foreign amino acid sequence may be an epitope.

The invention also relates to the mucin peptide produced by the method the above-described methods, which peptide may be 40, 60, 80 or, preferably, 105 amino acids in length, although longer lengths are possible.

In another embodiment, the present invention relates to an immunogenic composition capable of inducing in a mammal (such as a human or a mouse) antibodies against an epitope (such as a vaccine), which composition comprises a synthetic muc-1-like peptide. The present invention further relates to an immunogenic composition capable of inducing in a mammal (such as a human or a mouse) cytotoxic T cells (CTL) against an epitope (such as a vaccine), which composition comprises a synthetic muc-1-like peptide. The synthetic muc-1-like peptide comprises at least two 20-amino acid tandem repeats of muc-1 and is capable of attaining native conformation in the absence of glycosylation. The synthetic muc-1-like peptide may further comprise the amino acid sequence for an epitope. The synthetic muc-1-like peptide may be 40, 60, 80 or, preferably, 105 amino acids in length, although longer lengths are possible.

In a further embodiment, the present invention relates to a method of inhibiting an immune response in a mammal, comprising the step of administering the above-described immunogenic composition to a mammal in an immunogenically effective amount, which epitope is recognized by an autoantibody produced by the mammal.

In yet a further embodiment, the invention relates to a method of detecting the presence of antibodies to a specific disease (for instance, cancer such as pancreatic, breast or colon cancer) in a biological test sample, comprising the steps of:

a) contacting the above-described synthetic muc-1-like peptide containing an epitope with the biological test sample, which epitope is reactive with antibodies to the disease, under conditions such that a synthetic muc-1-like peptide-antibody complex is formed, and
b) detecting the formation of the synthetic muc-1-like peptide-antibody complex, which complex is indicative of the presence of antibodies to the specific disease.

In another embodiment, the invention relates to a method for inhibiting the growth of cancer cells, comprising the steps of:

a) obtaining antibodies to the tumor cells by injecting a test mammal, for example, a mouse or a rabbit, with the above-described synthetic muc-1-like peptide containing an epitope, which epitope is reactive with antibodies to the cancer cells, under conditions such that a synthetic muc-1-like peptide-antibody complex is formed, and isolating said antibodies from the complex from the mammal,
b) contacting the isolated antibodies from step a) with an agent capable of inhibiting the growth of cancer cells, under such conditions that an antibody-agent complex is formed, and
c) contacting the antibody-agent complex from step b) with cancer cells, under such conditions that the antibody-agent complex reacts with cancer cells and inhibits the growth of the cancer cells. The agent may be a radioisotope (for example, Yttrium 90 and Iodine 131), chemical (for example, methotrexate), toxin (for example, ricin or parts thereof), or enzyme.

In a further embodiment, the invention relates to a method for inhibiting the growth of pancreatic, breast or colon cancer cells, comprising the steps of:

a) obtaining antibodies to the tumor cells by contacting the above-described 105 amino acid synthetic muc-1- like peptide, with a biological test sample containing cancer cells corresponding to pancreatic, breast or colon cancer, under conditions such that a synthetic muc-1-like peptide-antibody complex is formed b) contacting the antibodies from step a) with with cancer cells, under such conditions that the antibodies react with the cancer cells and inhibit the growth of the cancer cells.

The invention also relates to a vaccine comprising a synthetic muc-1-like peptide of at least two 20-amino acid tandem repeats of muc-1 with the amino acid sequence for an epitope (corresponding to, for instance, a virus, a cancer or a bacteria) appropriately inserted to form a native synthetic antigen, wherein said synthetic muc-1-like peptide is capable of attaining native conformation in the absence of glycosylation. Preferably, the synthetic muc-1-like peptide is 105 amino acids in length and comprises at least five 20-amino acid tandem repeats of muc-1 with the amino acid sequence for an epitope appropriately inserted to form a native synthetic antigen. The synthetic muc-1-like peptide may comprise five sequential 20-amino acid tandem repeats of muc-1 and five additional amino acids, wherein said five additional amino acids are placed before or after the five sequential 20-amino acid tandem repeats.

The invention further relates to methods of producing immunity to a disease, such as a virus, a cancer or a bacterial infection, comprising the step of administering the vaccine to a mammal in an immunogenically effective amount.

The invention also relates to a vaccine comprising a synthetic muc-1-like peptide of 105 amino acids and an adjuvant, which muc-1-like peptide comprises at least five sequential 20-amino acid tandem repeats of muc-1 and five additional amino acids, and is capable of attaining native conformation in the absence of glycosylation. The five additional amino acids may be placed before or after the five sequential 20-amino acid tandem repeats.

The invention further relate to methods of producing immunity to pancreatic cancer, breast cancer or colon cancer, comprising the steps of administering the vaccine to a human in an immunogenically effective amount.

BRIEF DESCRIPTION OF THE DRAWINGS

FIG. 2 600-MHz cosy $^1$H-NMR spectra of muc-1 60 amino acid peptide dissolved in deuterated 0.1M phosphate buffer pH 7.2, in $D_2O$. The cross peaks show scalar correlation between amide-$^1$H and $^1H\alpha$. These amide protons are protected from exchange with the solvent by the folded structure of the mucin peptide.

DETAILED DESCRIPTION OF THE INVENTION

The invention is based in part on the discovery that an additional characteristic of the polyproline β-turn helix is the fidelity of synthesis to lengths not previously attained with Fmoc solid phase peptide synthesis (Fields et al., Principles and practice of solid-phase peptide synthesis. In Synthetic Peptides, G. A. Grant, eds., W. H. Freeman and Co., New York, pp. 77–183, 1992). Two additional characteristics of the poly-proline, β-turn helix are: (1) the ability to form an ordered long-lived conformation in solution and the protection of protons in while dissolved in $D_2O$ as determined by $^1$H-NMR spectroscopy (Fontenot et al., in press, 1993A & B); and (2) a large negative CD band at about 198 nm in aqueous solution. The absence of two separate negative CD bands at 220 nm and 208 nm and the lack of a positive band at 192 nm rules out α-helical character to either mucin, PRN60 or H2Dmuc7. In addition, no β-sheet structure is evident due to the absence of the negative band at 216 nm and the large positive band between 195 and 200 nm (Woody, Circular Dichoism of Peptides, In "The Peptides: Analysis, Synthesis, Biology," 7: 16–104, 1985; Johnson, Am. Rev. Biophys. Chem., 17: 145–166, 1988).

Previous model peptide studies with the tandem repeat peptide (PKLKL)n (see SEQ ID NO:5) concluded that a single negative CD band at 198 nm was indicative of random coil. However, Dukor & Keiderling (Biopolymers, 31: 1747–1761, 1991) have shown that small peptides tend to assume transient left-handed $3_1$-helices like that found in poly-proline II, which consists of all trans proline (Dukor & Keiderling, Biopolymers, 31: 1747–1761, 1991). Thus, "random coil" peptides display similar conformations and CD spectra as polyproline β-turn helixes but at much lower intensity as demonstrated in FIG. 10. Clearly, the large negative CD band indicates secondary structure rather than the absence of structure.

The two-dimensional $^1$H-NMR (COSY) experiment in $D_2O$ (an example is described below) using a 60 amino acid synthetic peptide shows that the mucin tandem repeat domain can fold into a stable structure, and that this structure is capable of sequestering protons from exchange by deuterium for more than 24 hours. In addition, one-dimensional $^1$H-NMR experiments in $D_2O$ with the synthetic peptide analogs corresponding to one-, two-, and three-repeats of the tandem repeat domain, show that formation of the structure is occurring with increasing number of repeats.

Figure 3:
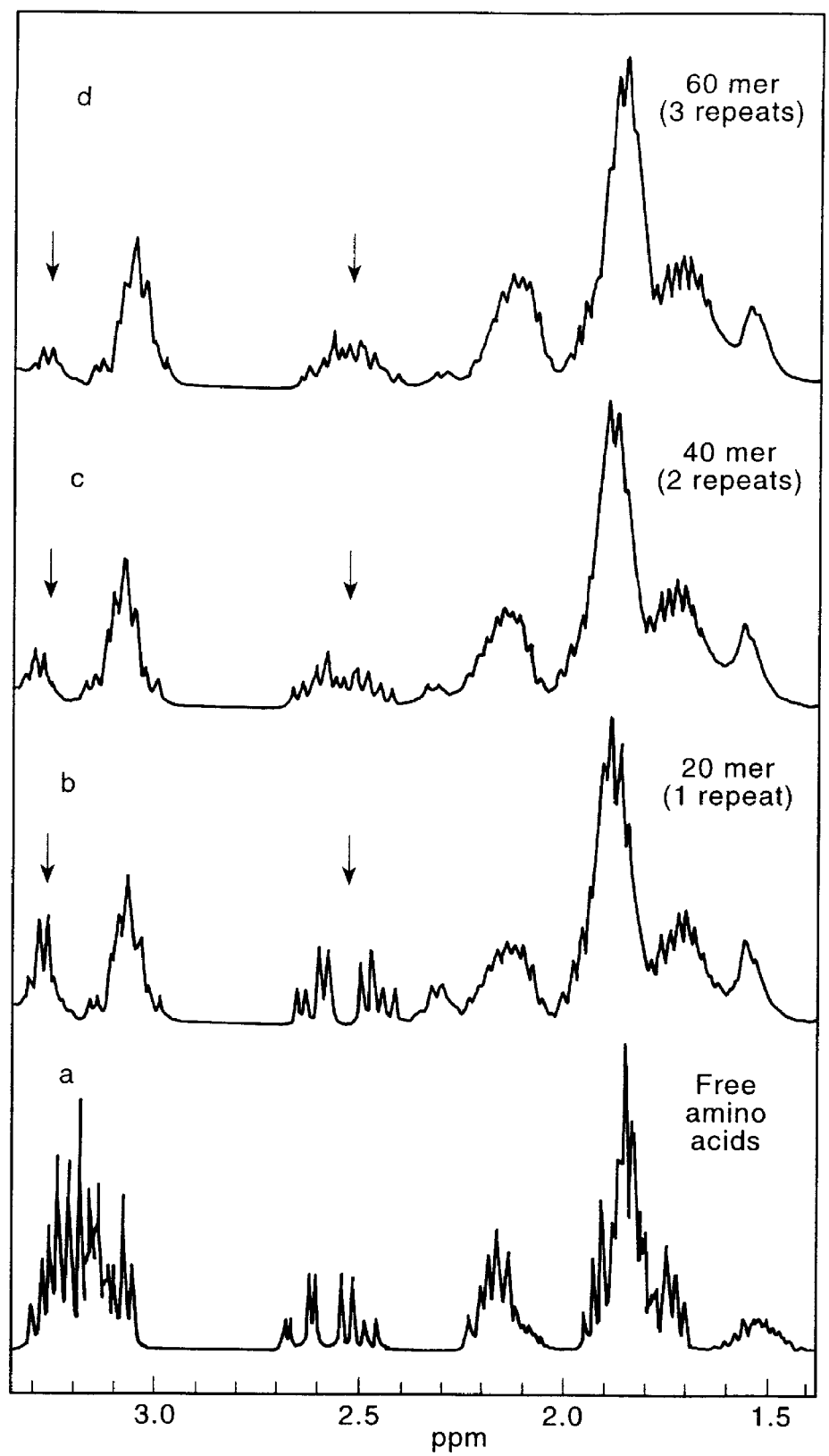
FIGS. 3A–3D $^1$H-NMR spectra of mucin peptides dissolved in deuterated 0.1M phosphate buffer pH 6.89, in $D_2O$ showing the region of the β-protons of aspartic acid and histidine. Development of structure depends on the number of tandem repeats in the peptide.
Figure 4:
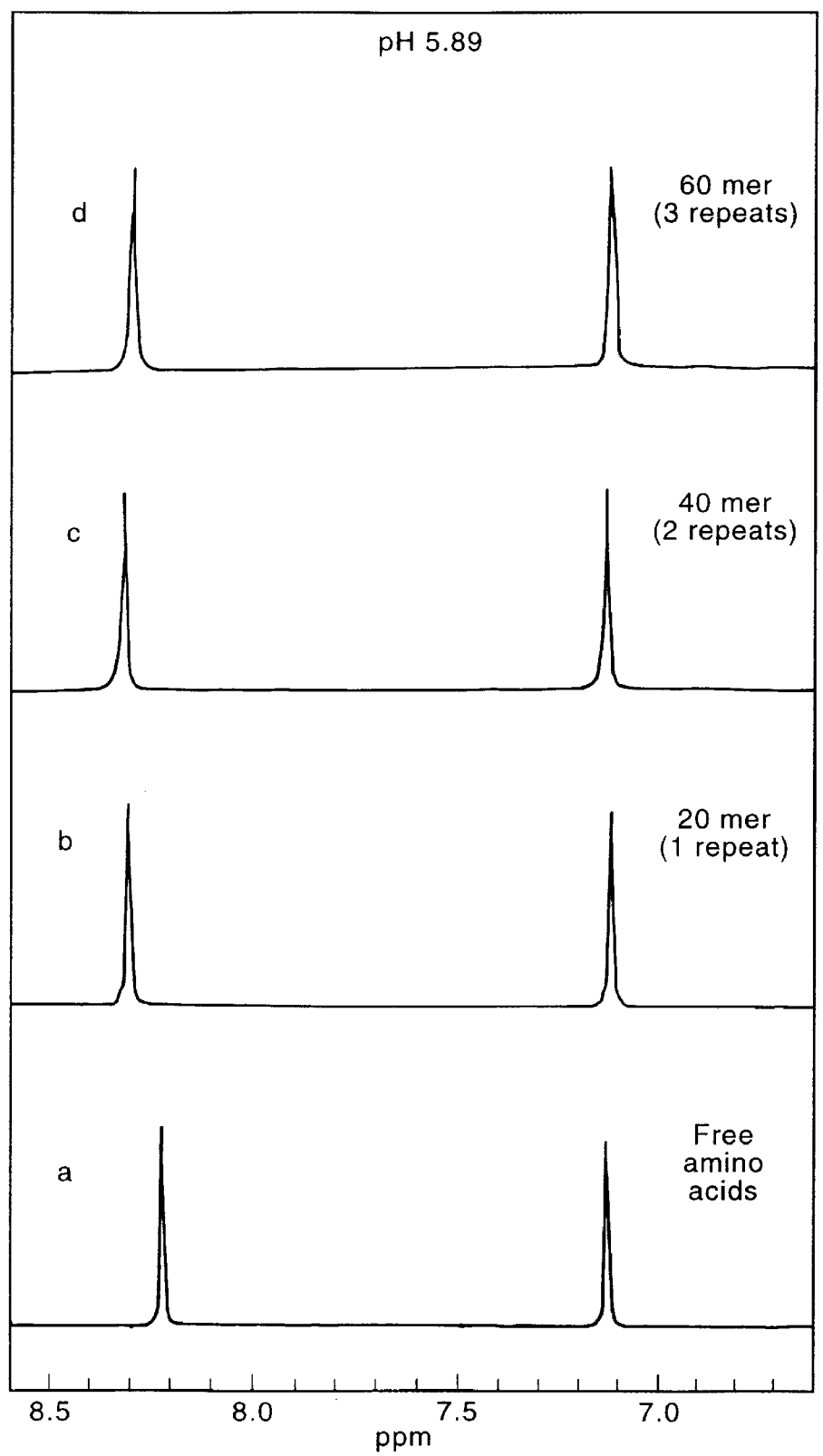
FIGS. 4A–4D $^1$H-NMR spectra of mucin peptides dissolved in deuterated 0.1M phosphate buffer pH 6.89, in $D_2O$ showing the region of the C2 (8.2–8.4 ppm) and C4.
Figure 5:
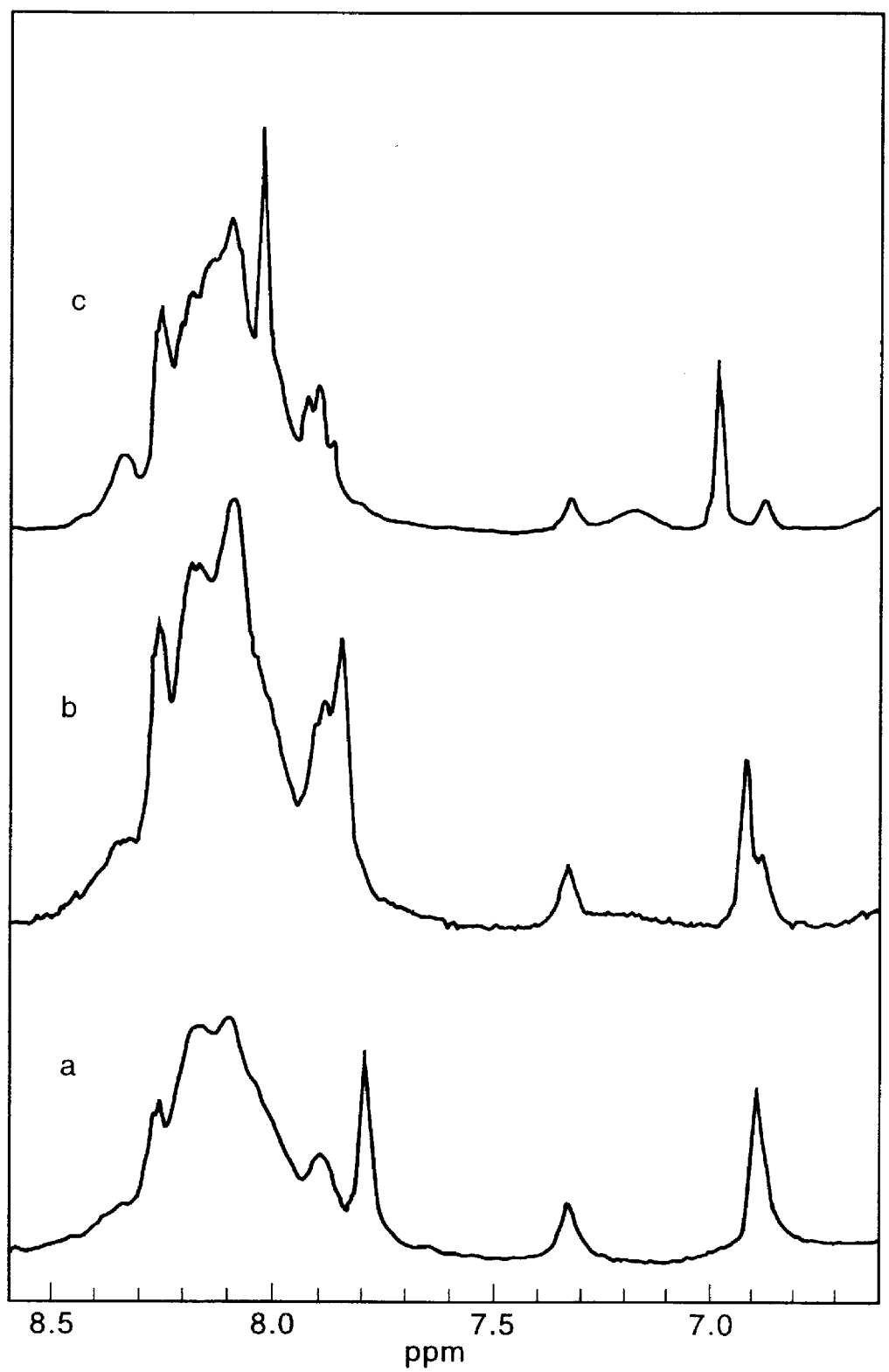
FIGS. 5A–5C $^1$H-NMR spectra of mucin peptides dissolved in $H_2O$ and 0.1M phosphate buffer pH 6.8. (A) twenty amino acid peptide corresponding to one tandem repeat. (B) Forty amino acid peptide corresponding to two tandem repeats. Sixty amino acid peptide corresponding to three tandem repeats.
Figure 6:
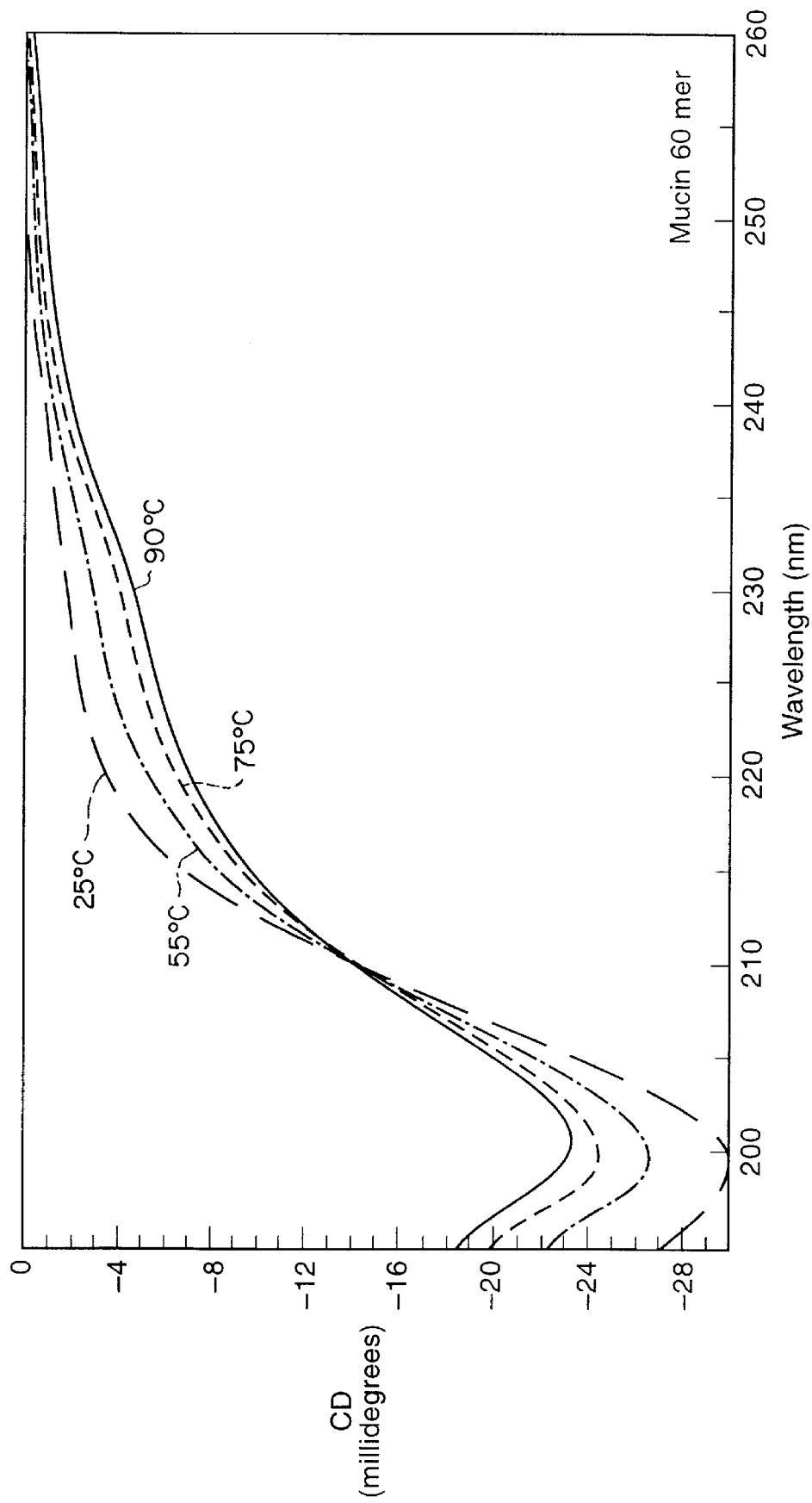
FIG. 6 Circular dichroism spectrum of mucin 60 amino acid peptide in 0.01M phosphate buffer pH 7.2 at 25, 55, 75 and 90° C.

The structural changes appear to be occurring throughout the length of the 20 amino acid repeat domain, as changes can be detected throughout the molecule by focusing on the β-protons in the region of 2.4 to 3.3 ppm from DSS (FIG. 3). By concentrating on the β-protons, the inventors have taken advantage of the peculiar repetitive nature of this protein domain. One twenty-amino acid peptide contains all of the protons that can contribute to the $^1$HNMR spectrum and any differences observed in the spectrum of peptides corresponding to one-, two-, or three-tandem repeats can only be attributed to changes in the local magnetic environment imposed through the development of secondary structure along the polypeptide backbone. Clearly, the $^1$H-NMR spectra reveal that the structures of peptides containing one-, two-, and three-repeats are different. Yet, peptides containing multiple histidyl residues whose C2 and C4 resonances resolve into single peaks suggests that the environment of each histidine in multiple repeat peptides are equivalent. It is believed that the $^1$H-NMR results show that the precise conformation of a residue depends on the number of repeats in the peptide.

Previous studies on muc-1 core structure, using an 11-amino acid fragment of muc-1 tandem repeat, were able to show that a reverse-turn structure formed when dissolved in dimethyl sulfoxide, from D2 through P4, and that P4 existed in the trans conformation (Tendler, 1990 and Scanlon, et al., 1992). Using much larger synthetic peptides, the inventors have demonstrated that there is a gradation of structures that depends on the size of the peptide.

This data is strongly supported by the monoclonal antibody binding data. Many of the monoclonal antibodies failed to react with a peptide corresponding to just one repeat, even when the epitope was present, but increasing number of repeats resulted in increased antibody reactivity. This behavior is consistent with that found by other authors which show that providing amino acids C-terminal to the first proline forms the major immunodominant epitope (Price, et al., Molecular Immunology, 27: 795–802, 1990 and Xing, et al., Immunology, 72: 304–311, 1991).

The $^1$H-NMR experiments described below clearly show that the mucin tandem repeat domain assumes an ordered structure in solution, and the form of the structure may be further understood by analysis of the mucin sequence, the shape of the molecule obtained from intrinsic viscosity measurements and electron microscopy, and the circular dichroism studies.

In one embodiment, the invention relates to synthetic muc-1 peptides comprising at least two 20-amino acid tandem repeats of muc-1, which synthetic muc-1 peptide is capable of attaining native conformation in the absence of glycosylation. For instance, the muc-1 peptide may comprise 2, 3, 4, 5 or more tandem repeats of muc-1. The synthetic muc-1 peptides of the present invention may be 40, 60, 80 or, preferably, 105 amino acids in length, or even longer, and may be covalently linked to a pharmaceutically acceptable carrier molecule or adjuvant, and may be part of a kit comprising the synthetic muc-1-like peptides and conventional reagents.

Peptide repeats which should be used are those that are poly-proline β-turn helixes. Some common characteristics of peptides having poly-proline β-turn helixes include:

1. Approximately 20–60% proline, and a high content of glycine, serine and glutamine;
2. Low predicted a-helix and b-sheet secondary structure content and a high predicted content of b-turns;
3. A circular dichroism spectrum consistent with high turn content and low a-helix and b-sheet secondary structure content;
4. Intrinsic viscosity values consistent with the formation of extended rod-shaped structures (Matsushima et al. Proteins: Structure, Function and Genetics 7:125–155, 1990).

Examples of sequences of peptides which can be synthesized by RaMPS are shown in Table 1. The naturally occurring mucin tandem repeat is shown in Table 1, No. 1. The entire proline rich neutralization domain of Feline leukemia virus and a 42 amino acid N-terminal fragment of this domain is shown in Table 1, No. 2, and 3 respectively. Other mucin peptides, such as muc-2, muc-3, or muc-6, are tandem repeats of various lengths. Although these mucin peptides do not have all the same characteristics of muc-1, regions of their sequences can be replaced, such as by proline. Thus, the natural length of the tandem repeat of each particular mucin may be preserved.

In another embodiment, the invention relates to a synthetic muc-1-like peptide that comprises at least two 20-amino acid tandem repeats of muc-1 and a foreign amino acid sequence, which peptide is capable of attaining native conformation in the absence of glycosylation. For instance, the muc-1-like peptide may comprise 2, 3, 4, 5 or more tandem repeats of muc-1. The foreign amino acid sequence may be an epitope, such as, for instance, an antigenic epitope corresponding to a virus (for example, HIV), a bacteria, a parasite, or cancer (for example, pancreatic cancer, breast cancer, ovarian cancer or colon cancer).

The synthetic muc-1-like peptides of the present invention may be 40, 60, 80 or, preferably, 105 amino acids in length, and may be covalently linked to a pharmaceutically acceptable carrier molecule or adjuvant, and may be part of a kit comprising the synthetic muc-1-like peptides and conventional reagents.

In a further embodiment, the present invention relates to a method of producing a mucin peptide having at least two tandem repeats, which peptide is capable of attaining native conformation in the absence of glycosylation. The method relates to standard solid state synthesis protocols, with several modifications.

Conventional methodology is employed with the following modifications. Synthesis is stopped when the primary sequence reaches 30 amino acids in length. One half of the resin-bound 30 amino acid peptide is then removed. A monitoring step is then employed to monitor the completeness of the reaction. Then, the reaction cycle is continued until the desired length of peptide is obtained.

The method comprises the steps of:
i) activating an amino acid of interest;
ii) introducing the activated amino acid of interest to appropriate solid phase;
iii) reacting under appropriate conditions until completion;
iv) monitoring for completeness of reaction;
v) repeating steps i) to iv) with the next amino acid of interest, until a 30 amino acid peptide is obtained, at which point half of the 30 amino acid peptide is removed; and
vi) continuing the reaction cycle until a mucin peptide of desired length having at least two tandem repeats and capable of attaining native conformation in the absence of glycosylation is formed.

By way of example, the method of the present invention may be achieved by the following protocol, using manual methodology on a Rapid Multiple Peptide Synthesizer (RaMPS).

The Coupling Reaction 0.25 mmole of the appropriate OPfp or Odhbt amino acid ester is dissolved in 1 ml of DMF and added to a standard RaMPS resin cartridge. 0.2 ml of 0.5M 1-hydroxybenzotriazole (HOBT) in DMF is added to the cartridge. 2 ml of DMF is used to rinse the remaining OPfp ester from the amino acid vial into the RaMPS resin cartridge. After the cartridge is capped securely, it is shaken for 2 hours at room temperature.

The RaMPS processor is then turned off, and the cartridge uncapped, opened and drained. The solvent is aspirated under a vacuum.

The resin is soaked for 30–45 sec with DMF, drained and aspirated. This is repeated twice. (3 cycles total)

Next, the resin is soaked for 30–45 sec with Methanol, drained, and aspirated. This is repeated. (2 cycles total)

Next, the reaction is monitored for completeness using the Kaiser or Isatin Test. If the coupling was incomplete, the next step is to be done and the first 4 steps are repeated (through the soaking of the resin in methanol for 30–45 seconds, draining and aspirating). If coupling was complete, the next step is to be done.

The resin is soaked for 30–45 sec with DMF, drained and aspirated. This is repeated three times. (4 cycles total)

The resin is then soaked 30–45 sec with 50% piperidine/DMF, and drained.

Then the RaMPS cartridge valve is closed, and 3 ml 50% piperidine/DMF is added. The cartridge is capped and shaken for 20 minutes. The cartridge is then drained.

Next, the RaMPS resin is soaked for 30–45 seconds with 100% DMF. drained and aspirated. This is repeated twice. (three cycles total)

A monitoring step is added at this point to detect incomplete deblocking reactions and to prevent human errors.

(If, at this point, the last amino acid has been coupled to the resin, cleavage of the completed peptide should be done next.)

RaMPS resin are then soaked for 30–45 sec with 100% methanol, drained and aspirated. This is repeated. (two cycles total)

RaMPS resin are soaked for 30–45 sec with 100% DMF, drained and aspirated. This is repeated three times. (four cycles total)

The next amino acid may then be added using the procedure outlined above, beginning with the first step.

After a length of 30 amino acids is reached, half of the resin is removed and placed in a separate cartridge. The concentration of amino acid is kept the same but the ratio of [AA/[Peptide chain on resin] is doubled.

Cleavage of the Completed Peptide

The RaMPS™ resin is soaked for 30–45 sec with 100% methanol, drained and aspirated. This is repeated twice. (3 cycles total).

The resin is aspirated for 10 minutes so that it will dry.

After the valve of the RaMPS cartridge is closed, the following is added: 2.85 ml trifluoroacetic acid (TFA); 135 ul phenol (H2O liquified) or thioanisole, as appropriate; 15 ul ethanedithiol.

The RaMPS cartridge is then capped and rocked at room temperature as noted.

| RapidAmide ™ resin | 16 hours |
| Wang resin | 3 hours |

Next, RaMPS cartridge is removed from the RaMPS processor and suspended over a 50-ml polypropylene tube.

The valve is opened, uncapped, and the solvent is drained into the tube.

The resin is next rinsed with 5.0 ml TFA, and drained into the tube. This is repeated.

The RaMPS cartridge may then be discarded.

The volume of TFA may then be reduced to 1–2 ml with a gentle stream of inert gas.

Next, 25 ml diethyl ether is added to the tube and mixed. The tube is then set on dry ice/aceton for 5 minutes or until the peptide precipitates.

The top ether layer may be removed and discard.

The previous two steps are to be repeated three times. (four cycles total)

Next, 25 ml ethyl acetate/diethyl ether (1.5:1) is added to the tube, and mixed. The tube is then set on dry ice/acetone for 5 minutes or until the peptide settles.

The top ether layer may be removed and discard.

The previous two steps are to be repeated. (two cycles total)

Next, 1.0 ml H$_2$O and 25 ml diethyl ether are added to the tube. The tube is then set on ice 5 minutes or until the layers separate. The top ether layer is discarded.

Any remaining ether is evaporated with gentle stream of inert gas.

The peptide may then be lyophilized from H$_2$O or put in a Speed-Vac.

The method of the present invention represents a breakthrough in the routine production of synthetic peptides of lengths 60 to 105 amino acids and greater, as long as native conformation structure in the absence of glycosylation is maintained. Typically, the efficiency of peptide synthesis decreases by 5% for each amino acid coupling past 20. (Grant, G. A., Evaluation of the Finished Product, in "Synthetic Peptides, A User's Guide" (1992), G. A. Grant eds., W. H. Freeman and Company, New York, pp. 185–258.) Therefore, with 5% error/per coupling, attempting to produce a peptide having 40 amino acids would result in none of the desired product.

Currently, the most common method to increase the efficiency for the production of longer peptides (for instance, peptides of 40 to 60 amino acids in length) is to perform two couplings of the same amino acid sequentially. Unfortunately, this results in increasing the error at a given step and the frequency of certain side reactions with difficult amino acid couplings. Consequently, the inventors were quite surprised at the efficiency with which they were able to produce mucin to 105 amino acids. The longest peptide previously produced by Fmoc synthesis was 86 amino acids. (Field et al., Principles and Practice of Solid-Phase Peptide Synthesis," in "Synthetic Peptides, A User's Guide" (1992), G. A. Grant, eds., W. H. Freeman and Company, New York, pp. 77–183.) In order for this to be accomplished, the fidelity of each step in synthesis had to be close to 100%. This can be achieved with engineered sequences as long as the proline content is relatively high (for instance, 15% or greater).

In another embodiment, the present invention relates to a method of producing mucin-like peptides having at least two tandem repeats and a foreign amino acid sequence, which mucin-like peptide is capable of attaining native conformation in the absence of glycosylation. The method relates to standard solid state synthesis protocols, with several modifications.

Conventional methodology is employed with the following modifications. Synthesis is stopped when the primary sequence reaches 30 amino acids in length. One half of the resin-bound 30 amino acid peptide is then removed. A monitoring step is then employed to monitor the completeness of the reaction. Then, the reaction cycle is continued until the desired length of peptide is obtained.

The method comprises the steps of:

i) activating an amino acid of interest;

ii) introducing the activated amino acid of interest to appropriate solid phase;

iii) reacting under appropriate conditions until completion;

iv) monitoring for completeness of reaction;

v) repeating steps i) to iv) with the next amino acid of interest, until a 30 amino acid peptide is obtained, at which point half of the 30 amino acid peptide is removed; and vi) continuing the reaction cycle until a mucin peptide of desired length having at least two tandem repeats and a foreign amino acid sequence, and is capable of attaining native conformation in the absence of glycosylation is formed.

By way of example, the above-described protocol may be employed to achieve the present invention.

The foreign amino acid sequence may be an epitope, such as, for instance an antigenic epitope corresponding to a virus (for example, HIV), a bacteria, or cancer (for example, pancreatic cancer, breast cancer, ovarian cancer or colon cancer). (Baehr et al., (1989) Mol. Microbiol. 3: 49–55) Epitopes which can be incorporated into the multiple tandem repeat synthetic peptide are shown in Table 2.

For example, T cell epitopes would be quite short, often only 3–4 amino acids in length. B-cell epitopes, on the other hand, are typically longer, although some can be as short as 3–5 amino acids.

The invention also relates to the mucin peptides produced by the above-described methods, which peptides may be 40, 60, 80 or, preferably, 105 amino acids in length, although longer lengths are possible as long as the secondary structure is not disrupted.

In addition, the invention presents practical methodology for producing a class of synthetic peptides that contain important antigens for vaccine and diagnostic development for human cancers and infectious diseases (Finn, Biotherapy 4:239–249 (1992)). The poly-proline helix offers a potential framework structure for designing new antigens by tandemly repeating important B- or T- cell epitopes or coupling of B- and T-cell epitopes to produce antigens of larger sizes.

Thus, in another embodiment, the present invention relates to an immunogenic composition or molecule capable of inducing in a mammal antibodies against an epitope (such as a vaccine), which composition or molecule comprises a synthetic muc-1-like peptide. The synthetic muc-1-like peptide comprises at least two 20-amino acid tandem repeats of muc-1 and the amino acid sequence for the epitope, and the synthetic muc-1-like peptide is capable of attaining native conformation in the absence of glycosylation. The synthetic muc-1-like peptide may comprise 2, 3, 4, 5 or more muc-1 tandem repeats, and may be 40, 60, 80 or, preferably, 105 amino acids in length, although longer lengths are possible. The immunogenic molecule can be administered with an adjuvant.

Mucin tandem repeat polypeptide core region is immunogenic and HLA-unrestricted because it has a secondary structure rich in prolines, which is stable, assumes native configuration, is a structural, not only a sequence repeat, and due to all of this is capable of direct binding and cross-linking of T cell and B cell antigen receptors. For instance, by the methods of the present invention, a synthetic peptide may be produced, 105 amino acids in length, containing 5 tandem repeats of 20 amino acids in length each, and five amino acids (such as, for instance, GVTSA (see SEQ ID NO:6), which may be placed on the back end or, preferably, the front end of the peptide). The longest mucin synthetic peptide reported to date has two repeats; more than two tandem repeats are critical for the peptide to assume a native structure and thus react properly with antibodies, to induce proper antibodies, and to stimulate cellular immunity.

This method of synthesis which is especially effective for peptides with characteristically placed prolines. Furthermore, the present invention can be utilized for synthesis of other very long peptides in which a particular short sequence can be synthesized on a long mucin-like backbone which can give the peptides a more native configuration and desired reactivity with antibodies or cells of the immune system. The synthesis of complex peptides using a polyproline β-turn helix structural motif constitutes a novel synthetic strategy that can produce remarkably high levels of efficiency and precision in the synthesis of exceedingly large peptides (for instance, longer than 40 amino acids).

The 105 amino acid long synthetic mucin peptide can be used as a tumor specific vaccine for patients with pancreatic, breast, ovarian and colon cancers. Previous studies have shown that epitopes on the mucin polypeptide core are targets for tumor specific cytotoxic T cells, and that their immunogenicity depends on several of them being tandemly repeated. These epitopes are present on the 105 amino acid synthetic peptide and tandemly repeated 5 times. Immunization of mice with this peptide in soluble form and with incomplete Freunds adjuvant generates a desired cellular immunity. This has not been achieved previously with short synthetic peptides. The length of the peptide which allows for the native structure to form, and the tandemly repeating epitopes are novel characteristics of this molecule and may be responsible for its immunogenicity.

Although the CDNA sequence of the mucin gene was available, the use of a tandemly repeated epitope for MHC-unrestricted stimulation of the immune response was not predictable. It is a novel discovery that a structurally stable, tandemly repeated molecule, which contains important immunogenic amino acid residues derived from any antigen (bacterial, viral, tumor, autoantigen) will be capable of eliciting an immune response in all individuals, independent of their HLA (MHC) molecules. Furthermore, the technique for successfully synthesizing these long tandem repeat peptides is novel as well.

The mucin structure may be used as the prototype of such a structure. An example is shown below:

---

MUCIN (see SEQ ID NO: 7)

A P D T R P A P G S T A P P A H G V T S A P D T R P
A P G S T A P P A H G V T S
A HYPOTHETICAL IMMUNOGEN (see SEQ ID NO: 8)
(e.g. viral epitope, bacterial epitope, autoantigen)

X P X X X P X P G S T A P P A H G V T S A P X X X P
X P G S T A P P A H G V T S

---

The multiple prolines are necessary for maintaining the rigid structure, even though their exact position may not have to be maintained. The sequence DTR in the mucin, located between the first two prolines in each repeat, is the target of the anti-mucin immune response. The rest of the sequence is inert for purposes of an immune response and can be left unchanged to serve as scaffolding, which further maintains the three dimensional structure. The DTR sequence can be substituted by a sequence from a virus, tumor antigen or autoantigen.

In general, the substitution sequence is a short peptide (for instance, about 3 amino acids long), in which only two or three amino acids are capable of contacting a T cell receptor for recognition by the immune system. The short peptide may, for instance, be derived from a long peptide bound to HLA.

Because most of these short amino acid sequences do not have a stable structure, they must bind to an HLA molecule in order to be presented to the immune system. This binding is very specific and depends on a specific type (allele) of an HLA molecule. Thus when an immunogenic sequence is identified by its ability to stimulate immune response in some individuals, there will be other individuals with different HLA types such that their immune system will not be stimulated by it. This dependence on HLA is known as HLA restriction and it is a problem which must be overcome in designing peptide-based vaccines. The mucin-like structure bypasses HLA-restriction and the need for peptide presentation by providing the necessary rigid, stable, and tandemly repeated structure capable of activating T cell receptors, B cell receptors and the immune system.

Multiple tandemly repeated mucin epitopes stimulate T-cells directly, independent of presentation by patients' HLA molecules. The long synthetic mucin peptide containing 5 or more tandem repeats is designed to stimulate T cells directly. This is very significant, as peptide vaccines are usually restricted in use by the HLA type of a patient and its ability or inability to present the vaccine peptide. The long synthetic mucin peptide can be used as a vaccine in all patients. Furthermore, any immunogenic sequence superimposed on the mucin-like structure may be capable of stimulating an immune response in all subjects regardless of the HLA type.

The principles established with the long synthetic mucin peptide regarding the ability of tandemly repeated epitopes to stimulate immune responses independently of patients' HLA types, can be applied to other epitopes found in tumor antigens, in viral antigens, and in autoantigens. These epitopes are immunogenic only in a sub population of people with a particular HLA type capable of presenting them. Synthesizing these epitopes according to the mucin structure may render them independent of presentation by HLA molecules, and immunogenic in all individuals. Thus, one advantage of using the peptides of the present invention is their ability to induce a non-MHC-restricted immunogenic response in mammals regardless of their HLA type.

For instance, synthetic mucin peptide composed of five tandem repeats and 5 amino acids (such as, for instance, GVTSA, which may be placed on the back end or, preferably, the front end of the peptide), 105 amino acids long, may substitute for the native molecule as an immunogen. Thus, it is ideal for use as a synthetic vaccine. Synthetic mucin 105 peptide represents a prototype of a stable tandem repeat structure, onto which other immunogenic epitopes can be synthesized, and immune responses to them made HLA-unrestricted.

These immunogenic conjugates would be suitable for immunization against the disease whose antigenic epitope has been designed into the multiple tandem repeat synthetic peptide when administered in an immunogenically effective amount to a mammal, for example by the intradermal route.

Epitopes which can be incorporated into the multiple tandem repeat synthetic peptide include, for instance, an antigenic epitope corresponding to a virus (for example, HIV), a bacteria, or cancer (for example, pancreatic cancer, breast cancer, ovarian cancer or colon cancer). (See Table 2.)

In a further embodiment, the present invention relates to a method of inhibiting an immune response in a mammal, comprising the step of administering the above-described mucin-like peptide composition to a mammal in an immunogenically effective amount, which epitope is recognized by an autoantibody produced by the mammal. The mucin-like peptide will be recognized by the antibody and prevent its binding to the native target.

Vaccines of the instant invention, which, when administered to a mammal, induce a protective immunogenic response against the epitope present on the repeats, comprise one or more immunogenic mucin-like peptide, comprising a peptide with the disease-specific epitope, wherein each disease-specific epitope corresponds to a different portion of the epitope.

In addition, it is possible to produce a bivalent vaccine whereby immunogenic peptides described above, comprising synthetic peptides from epitopes of two different diseases, are mixed to form a single inoculum such that protective antibodies will be simultaneously raised in a mammal to both diseases.

As discussed above, the synthetic method of the invention is novel in that it achieves efficient and reliable synthesis of long peptides. There are a number of advantages associated with peptides of long length over the shorter peptides currently being synthesized. These advantages include, for instance, (1) the formation of native structure,
(2) the inclusion of more sequence and structural information within the same molecule,
(3) the fact that larger peptides make better antigens,
(4) the ability to cross link the antigen receptors of both B and T antigen receptors on the surface of immune system cells and directly induce either antibody production or T cell activation, and
(5) the development of high avidity type interactions between a given peptide substrate and multivalent antibodies (for diagnostic purposes).

With respect to the formation of native structure, the poly-reverse turn structure of this peptide motif may enable the use of the peptide for the development of vaccines. For a folded native protein, the backbone, which is composed of the linear sequence of amino acids, the chain traverses the hydrophobic interior of the protein and turns around at the surface using a reverse turn (or β-turn) to reverse the direction of the protein chain. The important antigens of bacteria and viruses are proteins and fold the same way, so a large portion of the surface of an antigen is composed of these turns.

Consequently, during an infection, antibody molecules, which are on the surface of B cells, first come into contact with the surface viral antigens, in their native fold, which are reverse turns. Turn structures are the easiest types of secondary structure to predict or to detect based on the sequence alone, without actually solving the structure of the protein. These structures are typified by the presence of proline and glycine. Many of the known neutralizing (protective) antibody binding sites of many viral and bacterial antigens are known or are believed to be these turn structures.

For example, the primary neutralizing determinant of HIV-1(the V3 loop), the virus that causes AIDS, contains the essential sequence GPGRAF. By all criteria of protein secondary structure prediction and by experimental determination, this sequence forms a reverse turn in the native protein. Antibodies to this structure are known to neutralize HIV-1 and hence protect from the pathogenic effects of the virus. This sequence can be substituted into the mucin sequence in the following way:

| | |
|---|---|
| MUCIN | P D T R P A P S T A P P A H G V T S A |
| HIV-MUCIN | G P G R A F P A P S T A P P A H G V T S A |
| OR | P D T R P A P S T A P P A G P G R A F |
| | (see SEQ ID NOS: 9–11, respectively) |

(see SEQ ID NOS:9–11, respectively). The synthetic production of these sequences in a repeating manner will produce a mucin-like molecule with multiple copies of the V3 loop in what may be the native turn structure. This peptide molecule may be used beneficially, such as in the following applications.

It has been shown that mucin-like molecules can induce IgM antibodies. IgM antibodies are pentavalent (5 copies joined together in a cylindrical manner) and therefore quite large. Thus, these antibodies may be excellent neutralizing antibodies. The huge size may be very effective in blocking the entry of the virus into the cell. Currently, none of the known neutralizing antibodies to HIV-1 are IgM, because only polyvalent antigens induce IgM.

Furthermore, IgM can be induced independently of T cells in an HLA unrestricted fashion. This would be advantageous to AIDS patients who are T-cell depleted and/or T-cell suppressed and are, therefore, unable to mount effective HLA restricted immune responses. A large poly-valent V3 loop antigen could be a very effective immunotherapeutic agent for HIV-positive people, and could significantly boost the immunity to the virus and slow or prevent the onset of AIDS in these hopeless people.

Longer peptides are also advantageous in that more sequence and structural information within the same molecule are included. For instance, additional sequences that code for T-cell epitopes could be inserted into the proline rich backbone and tandemly repeated to produce a mucin like molecule to induce antibodies in a T-cell dependent fashion or HLA-restricted fashion.

In addition, longer peptides make better antigens than shorter peptides. Furthermore, longer peptides exhibit the ability to cross link the antigen receptors of both B- and T-antigen receptors on the surface of immune system cells, and directly induce either antibody production or T-cell activation. Also, longer peptides would enable the development of avidity type interactions between a given peptide substrate and multivalent antibodies, which is useful in, for instance, diagnostic testing.

In addition to the use of these peptides as a vaccine, or as a component of a vaccine, the peptides of the present invention can also be used for diagnostic purposes. The presence and titers of antibodies to a specific disease in biological samples can be detected using synthetic peptides designed with the specific epitope for an immunogenic agent of the disease being measured.

Thus, in yet a further embodiment, the invention relates to a method of detecting the presence of antibodies to a specific disease (for instance, cancer, HIV, autoantibodies) in a biological test sample, comprising the steps of:

a) contacting the above-described synthetic muc-1 or muc-1-like peptide containing an epitope with the biological test sample (such as, for instance, serum or plasma), which epitope is reactive with antibodies to the disease, under conditions such that a synthetic muc-1 or muc-1-like peptide-antibody complex is formed, and
b) detecting the formation of the synthetic muc-1 or muc-1-like peptide-antibody complex, which complex is indicative of the presence of antibodies to the specific disease. These peptides can be used, for example, in a standard enzyme-linked immunosorbant assay (ELISA) or a radioimmunoassay (RIA) to detect the presence of antibody in biological samples.

In addition, the peptides may be used as a diagnostic reagent to evaluate patients' immune responses to their tumors pre- and post-immunization. For example, long synthetic mucin peptides may be a useful indicator of an ongoing immune response in patients with pancreatic, breast, ovarian, and colon cancers. The presence of anti-mucin antibody, before and after immunization, cannot be detected with short peptides, but is easily detectable when, for instance, the 105 amino acid peptide is used in ELISA. This peptide may be useful even in unimmunized patients for measuring the low level but existing immune response to the tumor. Thus, the peptide may be used for distinguishing between patients who are already responding to their tumor, and those who are not, which may significantly influence any decision regarding the course of treatment and prognosis of the patient's disease.

In view of the foregoing and the state of the art, it will be clear to those of ordinary skill in the art that disease specific test kits can be constructed for detecting antibodies to the desired disease in biological samples using techniques for detection that include ELISA, RIA, indirect immunofluorescence and Western blot analysis.

In another embodiment, the invention relates to a method for inhibiting the growth of cancer cells. The method comprises the steps of:
  a) obtaining antibodies to the tumor cells by injecting a test mammal using conventional techniques (for example, a mouse or a rabbit) with the above-described synthetic muc-1-like peptide containing an epitope, which epitope is reactive with antibodies to the cancer cells, under conditions such that a synthetic muc-1-like peptide-antibody complex is formed, and isolating said antibodies from the complex from the mammal,
  b) contacting the isolated antibodies from step a) with an agent capable of inhibiting the growth of cancer cells, under such conditions that an antibody-agent complex is formed, and
  c) contacting the antibody-agent complex from step b) with cancer cells, under such conditions that the antibody-agent complex reacts with cancer cells and inhibits the growth of the cancer cells.

The agent may be a radioisotope (for example, Yttrium 90 and Iodine 131), chemical (for example, methotrexate), toxin (for example, ricin or parts thereof), or enzyme.

The invention also relates to methods of inhibiting or blocking an immune response in a mammal. One and two tandem repeats, (i.e., 20 or 40 amino acids) maintain stable secondary structure and react well with specific monoclonal antibodies. In general, to stimulate the production of antibodies, peptides having several tandem repeats which can cross-link antigen receptors are required. However, since the shorter form maintains stable structure but is incapable of cross-linking receptors and activating the immune system, it may be used for blocking immune responses. This may be very important in autoimmunity and in transplantation.

Thus, in another embodiment, the invention relates to a method of inhibiting an immune response in a mammal, comprising the step of administering the above-described immunogenic composition to a mammal in an immunogenically effective amount, wherein the epitope is recognized by an autoantibody produced by the mammal.

Synthetic mucin tandem repeat peptides of only 20 or 40 amino acids do not stimulate immune responses because they cannot cross-link receptors. However, for purposes of inhibiting or blocking immune responses, various antigens or targets of an undesired immune response can be synthesized onto the mucin structure and used to block the interaction of the immune response with its natural target.

Target antigens in autoimmunity are not known yet. However, techniques now exist to begin to identify specific peptides involved in autoimmune responses. When these peptides are identified, two- or three-amino acid residues will also be identified that are specifically recognized by autoimmune T cells. These residues may be used to replace DTR or some other amino acids in the mucin short tandem repeat peptide. Because this peptide would be mucin-like, and thus structurally stable, it is expected to bind directly to the T cell and B cell receptors and antibodies and block their interaction with the target antigen.

An example of an autoimmune disease where this blocking strategy may be applied is rheumatoid arthritis. Even though the target antigen is not known, there is a very strong association of rheumatoid arthritis and the presence of HLA-Class II molecules which share all of the amino acid sequences, three amino acids long. These sequences are thought to be involved in presenting the antigen to T cells. By substituting the mucin DTR sequence by one of these amino acid sequences on a short synthetic tandem repeat peptide (20 or 40 amino acids) it may be possible to block autoimmune T cells.

All autoimmune diseases are characterized by the presence of autoantibodies. In many instances the precise targets of these antibodies are known. These antibodies could be prevented from binding to their targets with short mucin peptides carrying specific epitopes recognized by the antibodies.

In the present invention, long tandem repeat peptides (for example, 105 amino acids in length) are stimulatory because they not only bind but also cross-link receptors. Short (for example, 20 or 40 amino acids in length) are expected to block or inhibit an immune response because they bind but do not cross-link. In that way they can only interfere with binding to the real target.

The target antigen in graft rejection is the HLA molecule itself. It may be possible to use sequences which differ between the organ donor and the organ recipient HLA, synthesize them on the mucin structure and use to block cells or antibodies rejecting a transplanted organ.

The ability to synthesize long synthetic peptides with tandem repeat structure allowed the inventors to test the first ever synthetic peptide vaccine in cancer patients in a clinical trial which was conducted at the University of Pittsburgh. The vaccine consisted of 100 g of the 105 amino acids long mucin synthetic peptide which contains 5 tandem repeats, mixed with BCG adjuvant. The vaccine was administered as three subcutaneous injections, three weeks apart. The peptide was synthesized according to the above-described procedures. The clinical protocol was designed and approved by the University of Pittsburgh Institutional Review Board. The protocol was then submitted to the Food and Drug Administration, which after examining the specificity, identity, toxicity and safety experiments performed on the peptide, approved it as an investigational new drug (BB-IND 5114). Approval was granted to initiate a phase I/phase II trial on 60 cancer patients with advanced pancreatic, colon and breast cancers, who had failed all previous therapies. The trial was designed to test for possible toxicity, and the potential of the peptide to modulate immune response in vivo. In the sixty patients vaccinated so far no peptide related toxicities were observed.

The most important parameter the inventors were trying to achieve and measure was an increase in numbers of T cells capable of killing mucin expressing tumor cells. In the first four patients who completed the vaccination protocol, the number of cytotoxic T cells appeared to have doubled (Table 6).

As described above, long synthetic peptides can be used as diagnostic tools for detecting specific immune responses. In the clinical trials, the inventors have used this feature of a long tandemly repeated mucin peptide to detect anti-mucin, and therefore potentially anti-tumor antibody responses in sera of cancer patients. This same feature of the mucin peptide was used to measure pre- and post-vaccination antibody levels in vaccinated patients. As expected, about 10% of patients showed detectable antibodies, and again as expected from the design of the vaccine, the antibody response did not increase after vaccination (Table 7). The vaccine was designed to increase T cell immunity only.

An important observation in this initial trial was that the long mucin synthetic peptide can be used to measure the state of preexisting immunity in cancer patients. The inventors have performed skin tests by injecting 100 g of the 105mer peptide alone, which would cause a reaction only if the same molecule has been previously seen by the patient. Table 8 shows that virtually every patient responded to the peptide. The response was measured by biopsying the site of injection and growing the infiltrating T cells in vitro. This indicated that the same epitope previously seen on the patient's tumor, was properly mimicked by the synthetic peptide to induce a recall response. Fewer responses were observed against an equimolar mixture of short 9 amino acid mucin peptides which contained the main immunogenic epitope, 9mer(+PDTRP), and fewer yet to short peptides which excluded that epitope, 9mer(−PDTRP). Fewer responses are due to the HLA dependence for recognition of short peptides, such that not all patients can recognize them, only those which carry the correct HLA molecules. Of the 55 patients included in Table 8, 11 were non-responders, which illustrates their general suppressed state of immunity due to their disease. Tables 9, 10 and 11 give a more detailed evaluation of the response for each patient who responded to one or more peptides.

Several important points can be drawn from these results:

1. From the skin test results it is clear that the long synthetic peptide indeed mimics the native mucin molecule expressed on cancer cells. Patients immune system which has previously encountered this molecule on the tumor recognizes a corresponding immunogenic epitope on the synthetic peptide.

2. The inventors chose to first test the generation of immunity with the 105mer peptide in a mixture with a potent adjuvant BCG. Having the skin test results confirming the potential of the 105mer to be recognized by the immune system, several different forms of the vaccine may be designed based on the long peptide. Other adjuvants may be used, peptide concentration may be increased, the peptide may be administered in combination with various cytokines, etc.

3. The inventors have shown that the peptide can be used as a diagnostic tool to detect antimucin, and therefore anti-tumor immunity, both cellular (skin test), and humoral (antibody in ELISA assays).

The inventors proposed to assess immune response to mucin expressed in breast, colon and pancreatic tumors using the delayed type hypersensitivity (DTH) response to varied pools of nonameric long mucin peptides in patients with breast, colon or pancreatic carcinoma: 1) untreated patients, 2) patients completing therapy (post therapy) and without apparent disease and 3) patients with advanced, metastatic disease. This protocol was designed as a test of whether an immunologic response to pancreatic/breast/colon mucin peptides exists in vivo. In patients with pancreatic, colonic or breast malignancies, both antitumor or toxic side effects may be observed in patients tested for DTH but this is felt to be very unlikely. These will represent secondary goals of this protocol. Twenty patients with untreatable or metastatic disease will be immunized thrice at three weekly intervals and assessed for in vivo and in vitro immune reactivity.

Pancreatic, colonic and breast adenocarcinoma arise from malignant transformation of normal ductal epithelial cells. Both normal and transformed ductal epithelial cells express on their surface a large glycoprotein, mucin, which in normal cells is confined to the apical surface facing the duct. A certain number of mucin molecules are cleaved off the cell surface and can be found in ductal secretions. The directional expression of this molecule is lost in the tumor, and so is the architectural constraint of the normal duct, which results in the aberrant expression of mucin on the entire tumor cell surface, as well as its abnormal presence in the peripheral blood circulation. It thus becomes accessible to the immune system for recognition.

By characterizing cytotoxic specificity of T cell lines derived from pancreatic and breast cancer patients, the inventors identified the mucin molecule as the tumor antigen capable of stimulating patients' T cell immunity. The inventors further identified a peptide epitope on this molecule PDTRP, previously defined with a breast tumor specific monoclonal antibody, which serves as a target for tumor specific cytotoxic T cells (CTL). Normal mucin producing cells do not express this epitope. The presence or absence of this epitope correlates with the ability of mucin producing cells to be killed by tumor specific CTL. It is now known that this is a linear epitope present on the polypeptide core of the mucin, that it is cryptic on normal mucin, masked by glycosylation, and uncovered on malignant mucins due to incomplete glycosylation. There are several other peptide epitopes, detected by antibodies, which are preferentially expressed on tumor mucins due to incomplete glycosylation.

The goals of the clinical trial were to use a synthetic mucin peptide carrying tandemly repeated mucin epitopes as well as shorter peptides to evaluate the extent and frequency of mucin specific immune responses in patients with breast and pancreatic tumors, and the feasibility of inducing or intensifying these responses by injection of synthetic mucin peptides. The study demonstrated a more efficient anti-mucin immune responses which may lead to inhibition of tumor growth and prolonged survival.

Before developing any more complex immune stimulants such as recombinant vaccines, cytokine containing preparations, or preparations combined with bacterial adjuvants it was important to assess the presence (or absence) of detectable delayed type hypersensitivity (DTH) responses to this molecule. The ability of a synthetic mucin peptide to function as a vaccine was be tested as a vaccine in patients with otherwise untreatable colon or pancreatic cancer.
MHC-restricted and unrestricted recognition of mucin by T cells.

Mucin-specific T cells derived from either breast cancer patients or pancreatic cancer patients were capable of specific lysis of all tumors, but no other mucin producing tumors or normal mucin producing cells. The identity in the polypeptide core sequence of breast and pancreatic tumor mucins explained the unique specificity for those two tumors. Differential reactivity of normal and tumor mucins with several tumor-specific antibodies indicated differences in epitope expression which correlated with susceptibility to CTL lysis.

The perfectly conserved tandem repeat structure provided an explanation for the apparently MHC-unrestricted recognition of this molecule. MHC-unrestricted antigen specific activation of T cells, although uncommon, is not unique to mucins, but rather it may be a property of molecules and epitopes of certain defined characteristics. A T cell is activated through its antigen receptor either by antigen or anti-receptor antibody. Activation with anti-receptor antibody shows that receptor crosslinking is sufficient to activate a T cell. Multiple engagements and crosslinking of the TCR are highly unlikely events for most antigens. An efficient signal through a single receptor is thus delivered though the trimolecular, TCR/antigen/MHC complex, but only when this complex is made more stable by the accessory interactions of the CD4 and CD8 molecules with their MHC ligands. Most antigens alone do not, under normal circumstances, bind to the TCR with the sufficient affinity to activate a T cell. There are situations when this can be expected and has been seen to occur: 1) when the density of the antigen on the presenting cell is very high so that multiple T cell receptors can engage simultaneously, and 2) when the antigen is sufficiently large with numerous identical antigenic epitopes which can engage multiple receptors simultaneously. Mucin molecules fulfill both of these requirements.

Tumor specific epitopes on mucin molecules.

In order for mucins to serve as potential tumor specific antigens it must be supposed that mucins made by tumor cells are in some way distinct from mucin made by normal cells. Unique reactivity of breast tumor specific CTL for tumor but not normal mucin producing cells supports that possibility. It has been shown that the carbohydrate side chains of the tumor-produced mucins are shorter than the side chains of mucins produced by normal cells. There is also an indication that in tumor mucins not all of the potential glycosylation sites are used. This results in unmasking of otherwise cryptic protein core epitopes on tumor mucins which serve as tumor specific antigens. The same epitopes are concealed in normal mucins by complete glycosylation (Girling A, Bartkova J, Burchell J, et al. A core protein epitope of the polymorphic epithelial mucin detected by the monoclonal antibody SM-3 is selectively exposed in a range of primary carcinomas. Int. J. Cancer 43: 1072, 1989; Hanisch F-G, Uhlenbruck G, Peter-Katlinic J, Egge H, Dabrowski J and Dabrowski U. Structures of neutral O-linked polylactosaminoglycans on human skim milk mucins. J. Biol. Chem. 264: 872, 1989; Yan P-S, Ho S B, Itzkowitz S H, Byrd J C, Siddiqui B and Kim Y S. Expression of native and deglycosylated colon cancer mucin antigens in normal and malignant epithelial tissues. Laboratory Investigation 62: 698, 1990).

The inventors have further explored the expression of tumor specific epitope as a result of incomplete mucin glycosylation and have confirmed this phenomenon in a controlled experimental setting. This phenomenon can now be reproducibly caused to occur. With that in mind, non-glycosylated synthetic peptides were used to test the DTH reading and to immunize, allowing for synthetic maximal exposure of immunogenic epitopes.

Experiments performed to date in vitro provide evidence that patients with mucin producing adenocarcinomas have T cells capable of reacting with the tumor, and provide information regarding the nature of the tumor specific epitope(s) that can now be used as a basis for a rational vaccine design. Details of these findings can be summarized as follows:

1. Breast or pancreatic tumor-specific T cells (CD4+ and CD8+) can be isolated from regional lymph nodes of cancer patients and expanded to large numbers in vitro.
2. Both T cell populations react with epitopes on the mucin molecule.
3. One such epitope, the target for CTL activity, has been identified using an antibody SM3 which blocks CTL function and is specific for linear sequence PDTRP of the mucin 20 amino acid polypeptide core tandem repeat PDTRPAPGSTAPPAGHVTSA (see SEQ ID NO:12).
4. This epitope appears tumor specific, inasmuch as the T cells and the SM3 antibody do not recognize normal mucin producing cells.
5. Several other epitopes located on the polypeptide core are preferentially expressed on the tumor mucins and not on normal mucins.
6. The reason for the preferential expression of these epitopes is the aberrant glycosylation of the mucins in transformed cells.
7. Mucin cDNA expression vector drives high level of expression of mucin in EBV immortalized B cells, but this mucin is more glycosylated lacking some (e.g. SM3) and expressing lower levels of other tumor specific epitopes.
8. Inhibition of O-linked glycosylation in the transfected cells leads to the expression of SM3 and increased expression of other tumor specific epitopes, and to the ability of these cells to sustain specific proliferation of CTL and to be susceptible to CTL lysis (Kufe D, Inghirami M, Abe D, Hayes H, Justi-Wheeler H and Schlom J. Differential reactivity of a novel monoclonal antibody (DF3) with human malignant versus benign tumors. Hybridoma 3: 223, 1984; Hilkens J, Buijs F, Hilgers J, et al. Monoclonal antibodies against human milk-fat globule membranes detecting differentiation antigens of the mammary gland and its tumors. Int. J. Cancer 34: 197, 1984; Burchell J, Gendler S and Taylor-Papadimitriou J. Development and characterization of breast cancer reactive monoclonal antibodies directed to the core protein of the human milk mucin. Cancer res. 47: 5476, 1987).

The ability to dissect the precise immunogenic epitopes recognized by T-cells on other disease sites has only recently been possible (Hart M K, Weinhold K J, Scearce R M et al. Priming of anti-human immunodeficiency virus (HIV) CD8+ cytotoxic T cells in vivo by carrier-free HIV synthetic peptides. Proc. Natl. Acad. Sci 88: 9448–9452, 1991; Kast W M, Roux L, Curren J, et al. Protection against lethal Sendai virus infection by in vivo priming of virus-specific cytotoxic T lymphocytes with a free synthetic pentide. Proc. Natl. Acad. Sci. 88:2283–2287, 1991; Battegay M, Oehen S. Schulz M, Hengartner H, and Zinkernagel R M. Vaccination with a synthetic peptide modulates lymphocytic choriomeningitis virus-mediated immunopathology. J. Virol. 66:119–1201, 1992). This information has however been quickly applied in murine models in the 1991–1992 time frame to allow priming and protection in various viral disorders such as Sendai virus and lymphocytic choriomeningitis virus infections using short peptides as vaccines. The studies undertaken and described herein represented the first instance in which such approaches will be tested in humans and in cancer.

Immunogenicity of a long synthetic mucin peptide.

The inventors synthesized a mucin peptide which consists of five complete 20 amino acid tandem repeats plus 5 amino acids of the sixth repeat. In total this peptide contains six tandemly repeated T cell-stimulatory epitopes. Using NMR analysis and other biophysical measurements we have determined that this peptide assumes a native mucin structure capable of reacting with anti-mucin antibodies with a much higher avidity than a short peptide, and of stimulating T cell proliferation in vitro.

This long peptide was used to immunize Balb/C mice. 100 g of soluble peptide was administered intraperitoneally, mixed with incomplete Freunds adjuvant. The mice were boosted twice, at three week intervals. Seven days following the last boost the mice were tested for DTH by a footpad injection of 20 g of soluble peptide. A long synthetic peptide unrelated to mucin was injected into the contralateral footpad as control. Additional controls were unimmunized mice.

The swelling of the footpad was measured at 24, 48, 72 hours. The mice were also bled and anti-mucin antibody measured in the serum. DTH was observed in all mice previously immunized with the 105 amino acid peptide. Relatively low levels of antibody were detected, and mostly of the IgM isotype.

Mice immunized with a shorter, 20 amino acid long peptide containing only one repeat, and only one epitope, did not develop any immunity, and no DTH was observed even when tested with the 105 amino acid peptide.

The ability of this long synthetic peptide to elicit an immune response in soluble unconjugated form is very impressive. Even more impressive is its ability to preferentially induce cellular immunity over humoral immunity. Peptides conjugated to very immunogenic complex carrier proteins usually generate very high antibody level. The ability of both antibodies and CTL to recognize the same epitope suggests a possibility that antibodies, especially if produced preferentially and in larger amounts than specific T cells, could block the T cell reactivity against the tumors.

TABLE 12

Drugs: 3 Different Mucin Peptide Preparations
(see SEQ ID NOS: 13–28, respectively)

|   |   | Preparation |
|---|---|---|
| p 1–9 | PDTRPAPGS | 1 |
| p 2–10 | DTRPAPGST | 1 |
| p 3–11 | TRPAPGSTA | 1 |
| p 6–14 | APGSTAPPA | 2 |
| p 7–15 | PGSTAPPAH | 2 |
| p 8–16 | GSTAPPAHG | 2 |
| p 9–17 | STAPPAHGV | 2 |
| p 10–18 | TAPPAHGVT | 2 |
| p 11–19 | APPAHGVTS | 2 |
| p 12–20 | PPAHGVTSA | 2 |
| p 14–22 | AHGVTSAPD | 2 |
| p 15–23 | HGVTSAPDT | 1 |
| p 16–24 | GVTSAPDTR | 1 |
| p 18–26 | TSAPDTRPA | 1 |
| p 20–28 | APDTRPAPG | 1 |
| P105 | GVTSA (PDTRPAPGSTAPPAHGVTSA) x5 | 3 |

The following non-limiting examples illustrate the invention in more detail:

EXAMPLES

The following materials, methods and protocols were used in the examples below.

Peptide Synthesis.

Peptides were synthesized using manual methods on a Rapid Multiple Peptide Synthesizer (RaMPS) purchased from Dupont (Boston, Mass.). The syntheses were performed using 0.1 mM Rapid Amide (2,3-dimethoxybenzhydrylamine) resin cartridges purchased from Dupont (Boston, Mass.). The solvents N,N-dimethyl formamide (DMF) protein sequencing grade, methylene chloride (DCM) certified A.C.S. grade, and methanol Karl Fischer grade were purchased from Fischer Scientific (Fair Lawn, N.J.). The deprotection reagents of anhydrous piperidine and trifluoroacetic acid protein sequencing grade, were purchased Sigma (St. Louis, Mo.). The scavengers 1,2-ethanedithiol, thioanisole, and anisole were purchased from Dupont (Boston, Mass.).

The Fmoc amino acid side chain protecting groups were tert-butyl esters (OtBu) for aspartic and glutamic acid; tert-butyl ethers for serine, threonine, and tyrosine; 2,2,5,7,8-pentamethylchroman-6-sulfonyl (Pmc) for arginine; tert-Butyloxycarbonyl (Boc) for lysine; triphenylmethyl (trt) for histidine; and all Fmoc amino acids were purchased from Advanced Chem Tech (Louisville, Ky.). The amino acids were coupled as symmetric anhydrides for alanine, arginine, and histidine; active esters of pentafluorophenol for asparagine, aspartic acid, glutamic acid, glutamine, glycine, isoleucine, leucine, lysine, methionine, phenylalanine, proline, tryptophan, tyrosine, and valine (OPfp); active esters of 3-hydroxy-2,3-dihydro-4-oxo-benzotriazine (ODhbt) for serine and threonine; active esters of 1-hydroxybenzotriazole (HOBt) for histidine. The coupling times were a standard one hour at room temperature using 0.25 mmol OPfp and ODhbt activated amino amino acids and 0.1 mmol of HOBt in three ml DMF. Coupling reactions using 0.25 mmol of HOBt or symmetric anhydride activated amino acids were performed in 2 ml DMF and 1 ml DCM for one hour at room temperature. The peptide resins were split in half after a chain length of 30 amino acids was reached but the concentration of input amino acid for the newly separated fractions was maintained at 0.25 mmol per 3 ml of solvent. Ninhydrin reactions were performed at the completion of each coupling reaction using ninhydrin test kit reagents purchased from Dupont (Boston, Mass.).

The Fmoc Nα protecting group is removed at the completion of a synthetic cycle by shaking for 20 minutes in 3 ml 50:50 piperidine:DMF, followed by extensive washing with DMF and methanol. The side chain protecting groups and cleavage of the peptides from the resins were performed by shaking in 3 ml of 90:5:3:2, TFA: thioanisole: 1,2-ethanedithiol: anisole for 4 hours at room temperature in 5 ml poly-propylene Quik-Sep disposable chromatography columns from Isolab (Ackron, Ohio.). The TFA and peptide mixture was drained from the column into cold ethyl ether, followed by three sequential extractions with ethyl ether, three extractions with 60: 40 ethyl ether: ethyl acetate. Finally, the peptide is extracted into 3 ml of water and lyophilized.

Peptide Purification.

The crude peptide mixtures were purified by analytical reverse phase high pressure liquid chromatography (RP-HPLC) on a Waters 600E chromatograph, with a Waters 486 absorbance detector (Milford, Mass.) and a Linear 1200 series recorder from Cole Palmer (Chicago, Ill.). Analytical separations utilized a Delta Pak C18, 300 Å (3.9×300) mm RP-HPLC column and semi-preparative separations used a uBondaPak C18, (7.8×300) mm column from Waters (Milford, Ill.). Chromatography solvents were HPLC grade acetonitrile from Fisher Scientific (Fair Lawn, N.J.) and water both containing 0.1% TFA. The chromatographic separations were performed using a 1% per minute linear gradient of water (0.1% TFA) and acetonitrile (0.1% TFA). Initial conditions were 95:5. water: acetonitrile and final conditions were 40:60, water: acetonitrile.

Mass Spectrometry.

Electrospray ionization mass spectra were obtained using a Vestec electrospray source and model 201 single quadruple mass spectrometer (Vestec Corp., Houston, Tex.) fitted with a 2000 m/z range (1,2). Samples were delivered to the source in a 10 microliter injection loop at 5 microliters/min in 4% acetic acid: 50% acetonitrile.

Circular Dichroism.

The circular dichroism spectra were recorded on a Japan Spectroscopic Company (Jasco) model J-710 circular dichroism spectropolarimeter (Hachioji City, Japan). The temperature was controlled using a Jasco PTC-343 peltier-type thermostatic cell holder and temperature control program. The spectrum was recorded from 195–260 nm with readings every 0.1 nm at 25°, 55°, 75°, and 90° C. The peptide concentration was 0.1 mg/ml of HPLC purified peptide in 0.01M phosphate buffer at pH 7.2 except for the peptide H2D8 which was used at 1.0 mg/ml in 20:80, acetonitrile:phosphate buffer (0.01M pH 7.2). A 0.1-cm path length strain free quartz cuvette was used to record the spectrum. The solvent spectrum was subtracted from that of sample and a noise reduction subroutine was applied to the resultant spectrum. A total of ten scans were accumulated for each sample. No change in the solvent spectrum was observed with increasing temperature.

$^1$H-NMR Spectroscopy of TR Peptides.

$^1$H-NMR analyses was performed using HPLC purified and lyophilized peptides. The concentrations used were from 6–7.5 mM in 0.1M phosphate buffer, pH 5.9 with either $H_2O/D_2O$ (90%/10%) or $D_2O$ (99.9%). We chose to use a high ionic strength buffer to reduce the electrostatic interactions between molecules. A pH of 5.9 was chosen for the $D_2O$ studies to avoid perturbations of the spectra resulting from the partial protonation of histidine, but significantly different from the pKa value of histidine. The 1-dimensional $^1$H-NMR experiments in $H_2O$ were performed at pH 6.8.

A Bruker AM-500 NMR spectrometer equipped with Aspect 3000 computer and a 5-mm $^1$H probe was used to record the spectra of the mucin muc-1 peptides. The spectra were recorded at 25° C., with the temperature of the probe regulated with a BVT-1000 unit and calibrated with a methanol sample. The $D_2O$ spectra of the peptides were recorded 5 to 10 minutes after dissolution. Suppression of the water signal was accomplished during the repetition delay of 1.5 seconds for peptide samples in $D_2O$ and $H_2O$. The one-dimensional spectra were recorded following a single 90° pulse. A control spectrum of the $H_2O$ sample was taken without water presaturation to ensure that none of the amide protons were affected by presaturation of water signal at any given power level. A total of 1024 transients were collected for each spectrum. The two-dimensional correlated spectra (COSY) was recorded in a phase sensitive mode. A sine bell filter was applied to the time domain data in both F1 and F2. The acquired data size was 2048×1024 points. Zero filling was used to obtained a final data matrix of 4096×4096 points. All proton chemical shifts were relative to the reference compound 2,2-dimethyl-2-silapentane-5-sulfonate (DSS) at 0.0 ppm.

Intrinsic Viscosity.

All viscometry measurements were performed using a Cannon-Fenske-Ostwald type capillary viscometer with HPLC purified peptide in 0.1M phosphate buffer at pH 7.0 and 30° C. The procedure was as described previously (Tanford, et al., J. Am. Chem., 89:729–736, 1967 and Buzzell, et al., J. Phys. Chem. 60:1204–1207, 1956). The capillary constant was as calculated as reported by Tanford and Buzzell, 1956 (Tanford, et al., J. Phys. Chem. 60: 225–231, 1956). The kinematic viscosity measurements were repeated at least ten times, and the averages were used to calculate the intrinsic viscosity. Intrinsic viscosity was calculated from kinematic viscosity, and the appropriate density correction (0.0029 ml/g) was applied as recommended (Tanford, 1955). The Simha shape factor and the peptide axial ratios were calculated according to (Tanford, 1961 and Cantor, et al., 1980).

Molecular Modeling of the 60 Amino Acid Peptide.

The sequence of the tandem repeat (TR) domain of the human mucin muc-1 (Gendler, et al., PNAS USA, 84: 6060–6054, 1987) gene was modeled into a polytype I turn conformation on a silicon graphics model INDIGO (Mountain View, Calif.) terminal using the Tripos molecular graphics program SYBYL (St. Louis, Mo.). Using this model the longitudinal axis and cross sectional axis were measured, and the axial ratio (longitudinal/cross sectional) of the 60 amino acid peptide was estimated (Table III).

The TR domains of human mucins muc-1,2,3,4 were also modeled according to the rules of Chou and Fasman (1978) (Chou, et al., Ann. Rev. Biochem., 47: 251–276, 1978) for secondary structure prediction. Surface potential was predicted using the "Surface Plot" algorithm as described (Parker, et al., Biochemistry, 25: 5425–5431, 1986). Potential amphipathic alpha-helical regions were predicted using the "Amphi" algorithm of Margalit et al. (Margalit, et al., J. Immunol., 138: 2213–2229, 1987). The results of these analyses were used to construct conformational models (results not shown). The number of predicted turns per repeat is summarized in Table I.

EXAMPLE 1

Peptide Synthesis.

Sequences of peptides which were synthesized by RaMPS are shown in table 4. The naturally occurring mucin tandem repeat is shown in table 4, number 1. The entire proline rich neutralization domain of Feline leukemia virus and a 42 amino acid N-terminal fragment of this domain is shown in table 4, No. 2, and 3, respectively. The T-cell epitopes that were used to construct the engineered tandem repeat proteins and shown in table 4, No. 4, and 5 respectively.

Figure 8A:
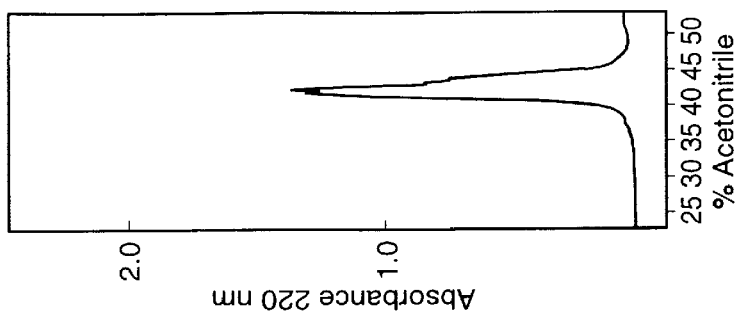
FIGS. 8A–8H The analytical HPLC chromatogram of the crude synthetic peptide products of (a) mucin 105 residues (b) PRN60, 60 residues (c) H2D8, 72 residues (d) H2DAS7, 70 residues (E) electrospray mass spectrum of the mucin 105 major fraction (f) electrospray mass spectrum of PRN60 major fraction (g) electrospray mass spectrum of H2D8 major fraction (h) electrospray mass spectrum of H2DAS7 major fraction.
Figure 8B:
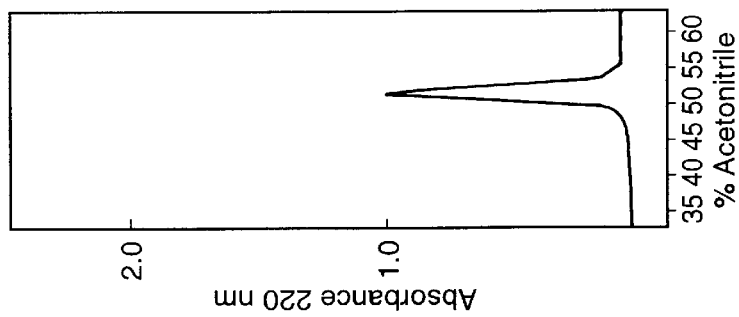
Figure 8C:
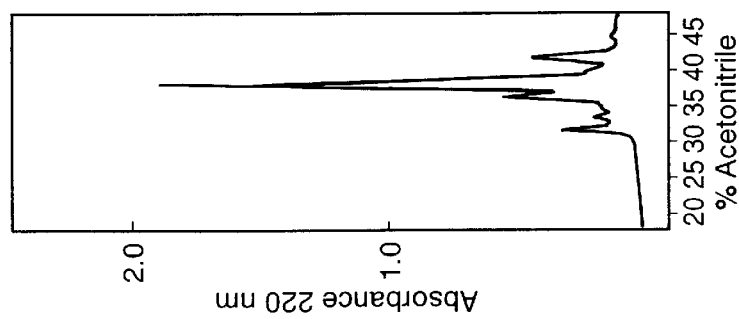
Figure 8D:
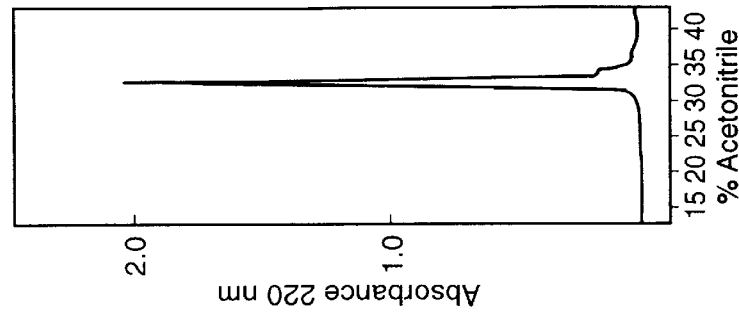
Figure 8H:
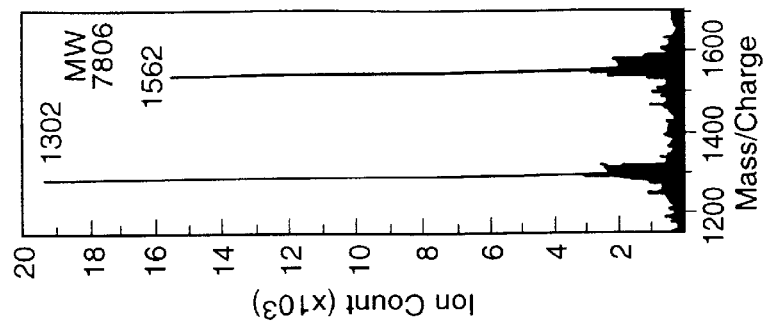
Figure 8G:
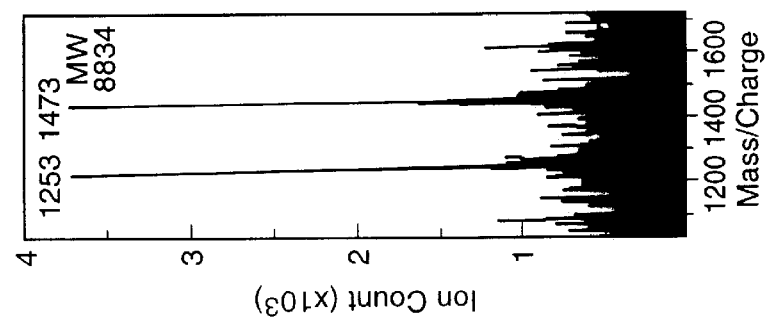
Figure 8F:
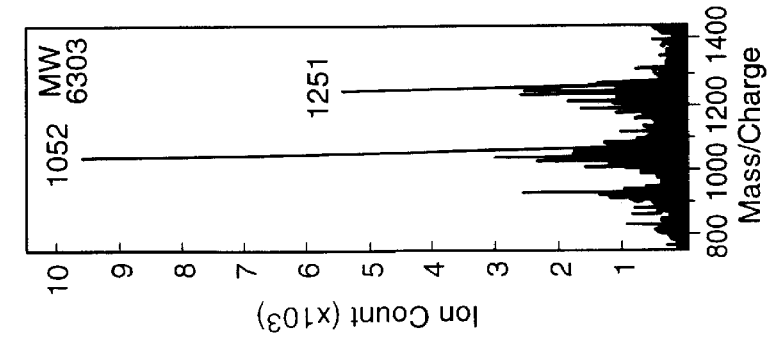
Figure 8E:
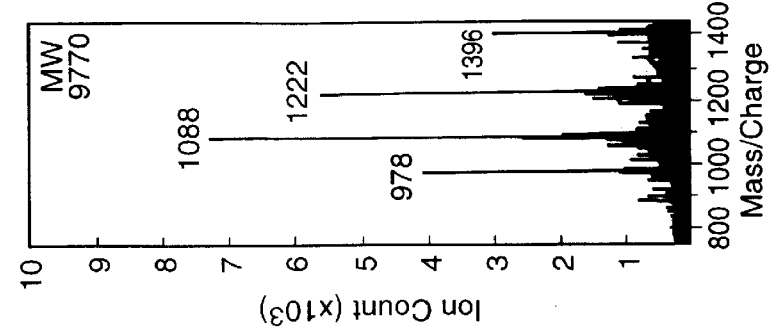

Using the human mucin muc-1 tandem repeat sequence as indicated in Table 4 we synthesized a series of peptides consisting of 1, 2, 3, 4, and 5.25 complete tandem repeats by manual solid phase peptide synthesis as described above. FIG. 8a shows the HPLC profile of the crude peptide products from the synthesis of the 105 amino acid mucin peptide. The electrospray mass spectrum (EMS) of the major fraction showing the correct molecular weight of 9770 daltons is shown below (FIG. 8e). The HPLC profile obtained with the 105 amino acid mucin peptide and the EMS are representative of the profiles from the syntheses of the 20, 40, 60, and 80 acid peptides corresponding to 1, 2, 3, and 4 tandem repeats of the human mucin muc-1 protein core. They all exhibited extraordinary efficiency and fidelity of synthesis. The expected molecular weight was obtained for each of the mucin peptide syntheses as shown in Table 5. Upon semi-preparative purification of the mucin peptides 85–92% recovery final product were typically obtained.

The synthesis of the entire 60 amino acid proline-rich domain of the feline leukemia virus external surface unit gp-70E (FeLV-PRN60) was also attempted by RaMPS. FIG. 8b shows the analytical HPLC profile of the crude synthetic products from this manual synthesis. The EMS of the major fraction (FIG. 8f) and Table 5 shows that the correct molecular weight was obtained. A related peptide (PRN42) corresponding to the N-terminal 42 amino acids of PRN60 (see Table 4) was also synthesized correctly as indicated by the molecular weight of the major fraction (Table 5). All other peptides that correspond to smaller analogs of PRN60 were synthesized with equal efficiency and fidelity.

Next was synthesized a peptide corresponding to a tandemly repeated nine amino acid T-cell epitope from the cytomegalovirus pp89 sequence early regulatory protein (H2D8) shown in Table 4. This peptide was previously identified as the optimal immunogenic CTL epitope in $H-2D^d$ mice (Reddehase, et al. Nature, 337: 651–653, 1992; Boyd, et al., PNAs USA, 89: 2242–2246, 1992). This peptide was selected because it contains two proline separated by three amino acids as found in the major immunodominant B and T cell epitope (PDTRP) (see SEQ ID NO:29) of the mucin tandem repeat (Barnd et al., PNAS USA, 86: 7159–7163, 1989; Jerome et al., Cancer Res. 51: 2908–2916, 1991). This peptide contains two proline residues per nine amino acids and is 22% proline. The HPLC profile of the crude synthetic 72 amino acid (H2D8) peptide containing eight tandem repeats is shown in FIG. 8c. The H2D8 peptide differs greatly from the mucin and FeLV peptides in hydrophobicity. The EMS results of the major HPLC fraction demonstrate that the correct peptide was obtained (FIG. 8g). A peptide corresponding to 5 tandem repeats showed similar results (Table 5).

In order to reduce the hydrophobicity of H2D8 a serine was added to position 10 in the sequence and phenylalanine 4 was substituted to alanine to create H2Dmuc7. This peptide was synthesized through seven tandem repeats (Table 4). These modifications in H2Dmuc7 were shown to result in a peptide with markedly reduced hydrophobicity as demonstrated by the HPLC profile of the 70 amino acid (FIG. 8d). The EMS spectra of the primary fraction shows that the correct peptide was obtained (FIG. 8h).

Figure 9A:
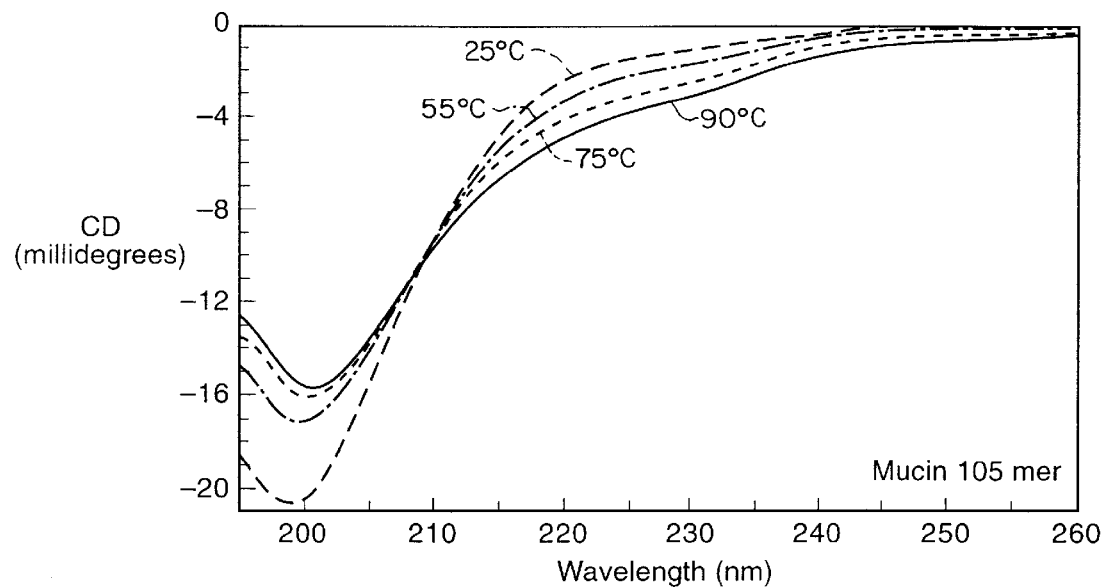
FIGS. 9A–9D Circular dichroism spectra of (a) mucin 105, (b) PRN60, (c) H2D8, (d) H2DAS7 at 25°, 55°, 75°, and 90° C.
Figure 9B:
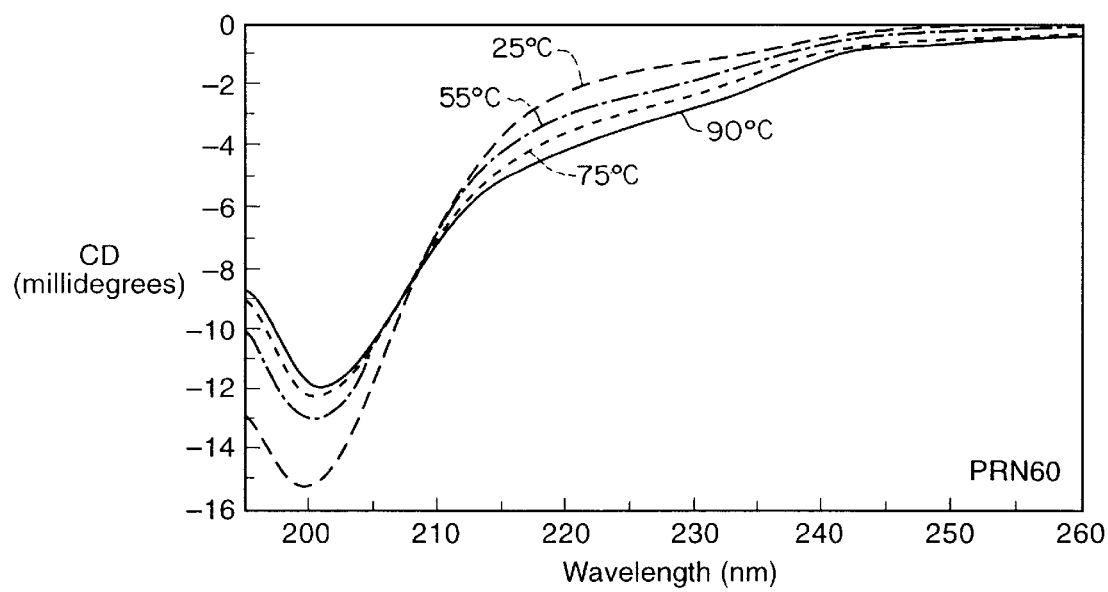
Figure 9C:
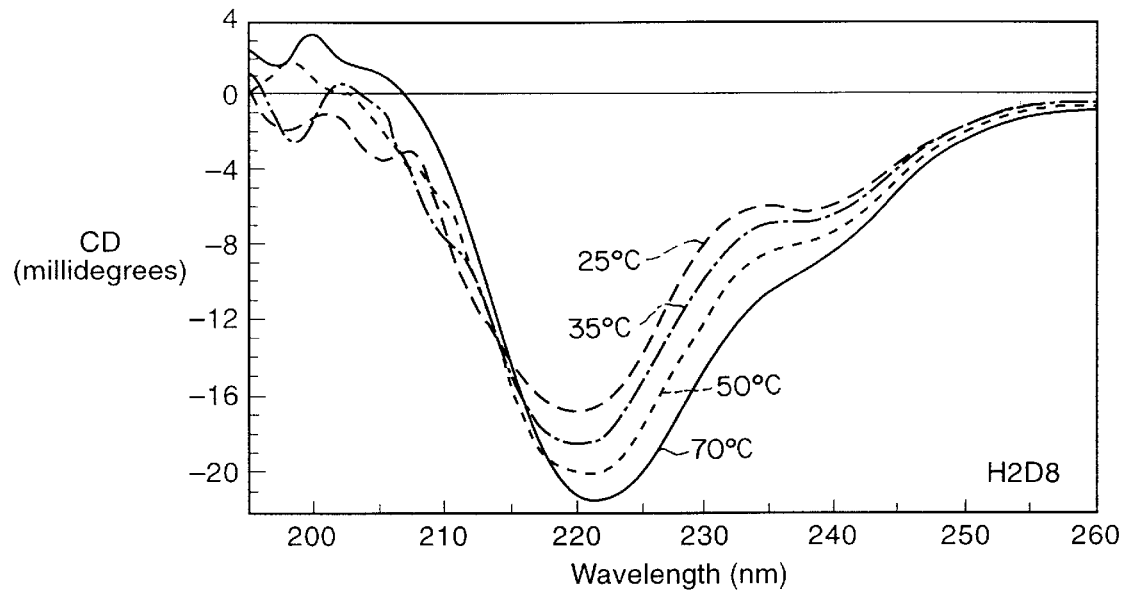
Figure 9D:
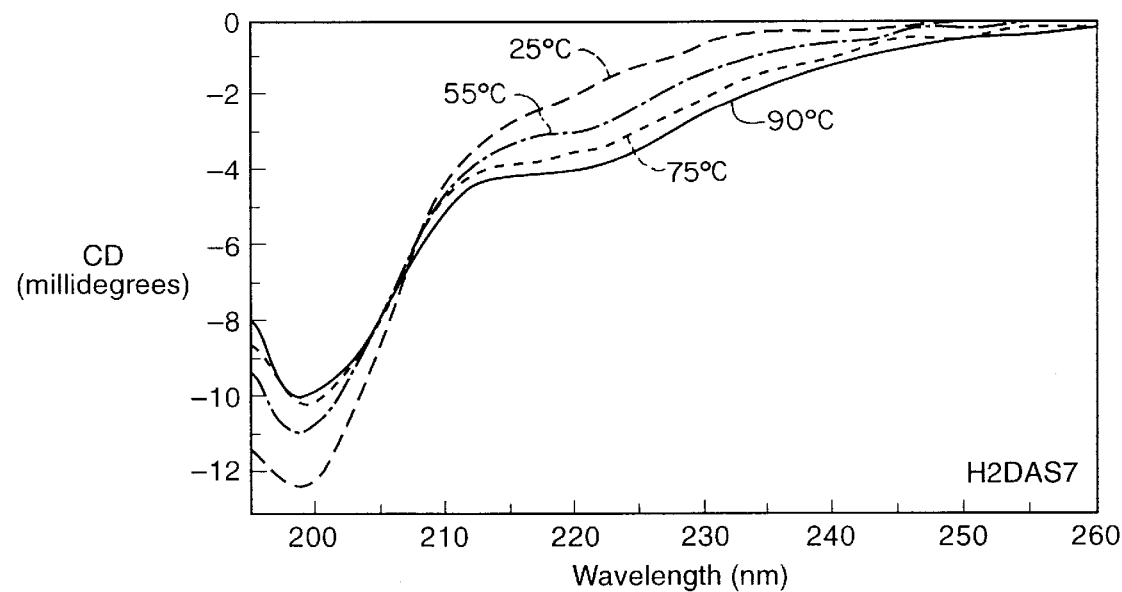

To investigate the possibility that the resulting peptide conformation can be correlated with the ease of synthesis, circular dichroism spectroscopy was performed on the HPLC purified peptides. The CD spectrum of the mucin 105 amino acid peptide is shown in FIG. 9a. The large negative peak at 198 nm is characteristic of proline rich proteins known to form extended structures including bovine elastin (Urry, J. Prot. Chem., 7: 1–34, 1987), C hordein (Tatham et al., Biochem. J., 226: 557–562, 1985), and collagen and poly-proline II (Madison and Schellman, Biopolymers, 9:511–567, 1970b). The spectrum observed with feline leukemia virus PRN60 (FIG. 9b) is identical with that obtained for mucin. Due to hydrophobicity (H2D8) was not soluble in 0.01M phosphate buffer at pH 7.2 and the spectrum of the tandemly repeated T-cell epitope peptide was acquired in 20:80, acetonitrile: phosphate buffer. The spectrum consists of a large negative peak at 222 nm and a smaller negative band at 238 nm. The CD spectrum of the modified H2D8 peptide (H2Dmuc7) was acquired in phosphate buffer and is shown in FIG. 9d. This spectrum is similar to that obtained for mucin and PRN60 with a large negative CD band at 198 nm.

The large negative CD band at 198 nm is identical with that obtained for the model proline compound N-acetyl-L-proline-N,N-dimethylamide (AcProDMA) (Madison and Schellman, Biopolymers, 9:511–588, 1970 b & c). The large negative CD band at 198 nm for AcProDMA in aqueous solution was shown to be due to three $\pi-\pi^*$ transitions and a large $\pi-\pi^*$ transition in the tertiary amide and was shown to be characteristic of proline in the trans conformation (Madison and Schellman, Biopolymer, 9:511–588, 1970 b & c). The CD spectrum of AcProDMA in the cis conformation is favored in hydrophobic environments and results in a positive band at 198 nm and the resultant spectrum of a mixture of cis and trans isomers could be represented by a linear combination of the two spectra (Madison and Schellman, Biopolymers, 9:65–94, 511–567, 1970 a & b).

To see whether the negative CD band at 198 nm is due to cis and trans proline isomers or conformational effects, the inventors tested the possibility that increasing the temperature would decrease the CD intensity at 198 nm. The CD spectra were recorded at 25°, 55°, 75°, and 90° C. FIGS. 8a, b, and d show that the CD intensity at 198 nm in 0.01M phosphate buffer at pH7.2 was decreased at 90° C. as compared to 25° C. by 33% for mucin 105, 29% for PRN60, and by 22% for H2Dmuc7. In contrast, the CD intensity of the shoulder region from 215 to about 240 nm increases for all the peptides with increasing temperature. The set of temperature curves for mucin, PRN60, and H2Dmuc7 exhibit isocircular dichroic points at 208, 209, and 207 nm (FIGS. 9a, b, and d). This suggests the existence of two discreet populations, one at high and one at low temperatures (Tatham et al., Biochem, J., 226: 557–562, 1984). The CD spectrum of H2D8 (FIG. 9c) was recorded at 10 fold higher concentration and was devoid of the large negative peak at 198 nm. This suggests that in 20% acetonitrile this peptide contains proline in the cis conformation. The remainder of the spectrum of H2D8 from behaved like the shoulder region of mucin, PRN60 and H2Dmuc7 with increasing temperature.

Figure 10:
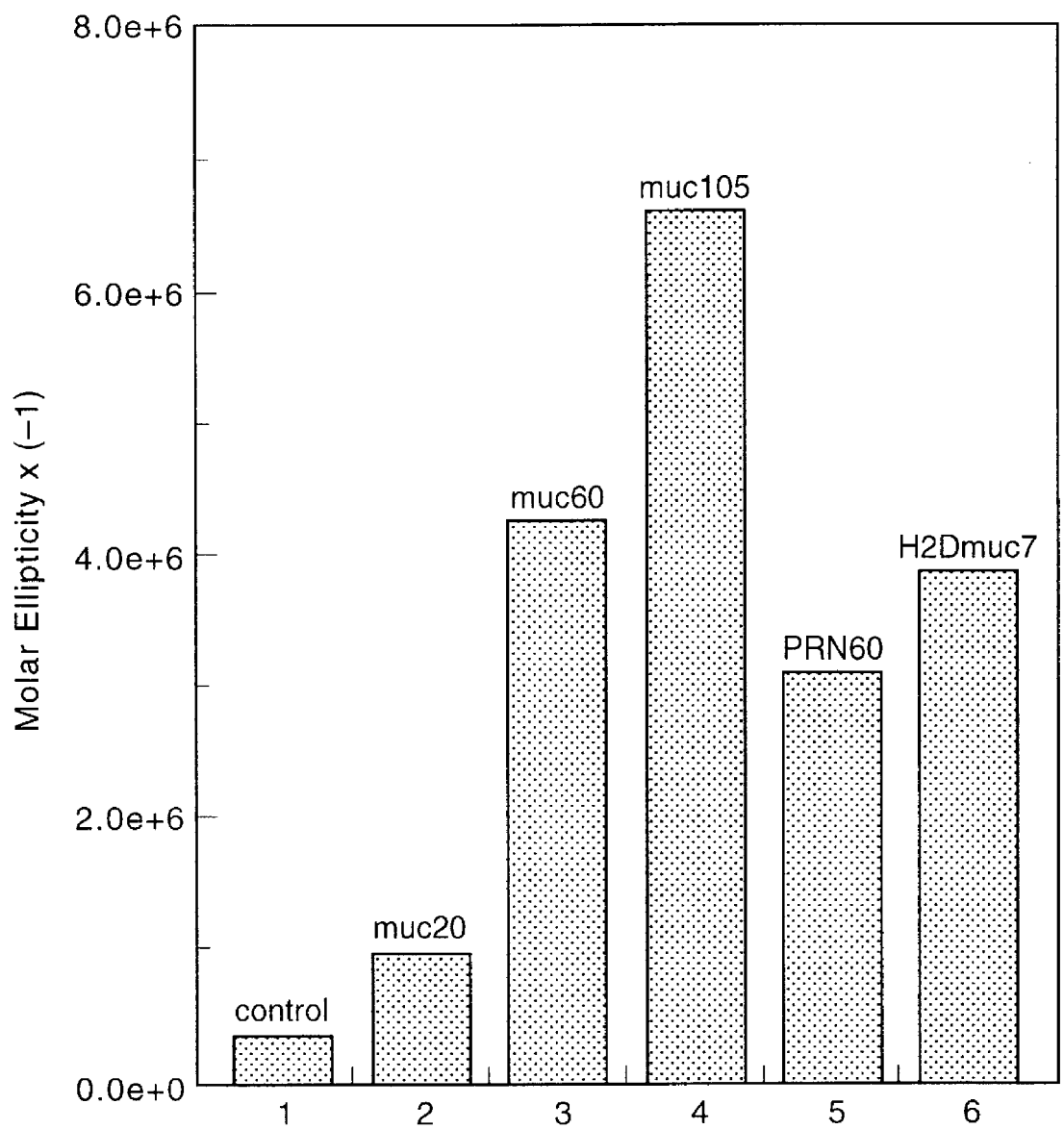
FIG. 10 The molar ellipticity [Θ] of (1) control peptide (2) mucin 20 residues (3) mucin 60 residues (4) mucin 105 residues, (5) PRN60, (6) H2DAS7 at 25° C.
Figure 11:
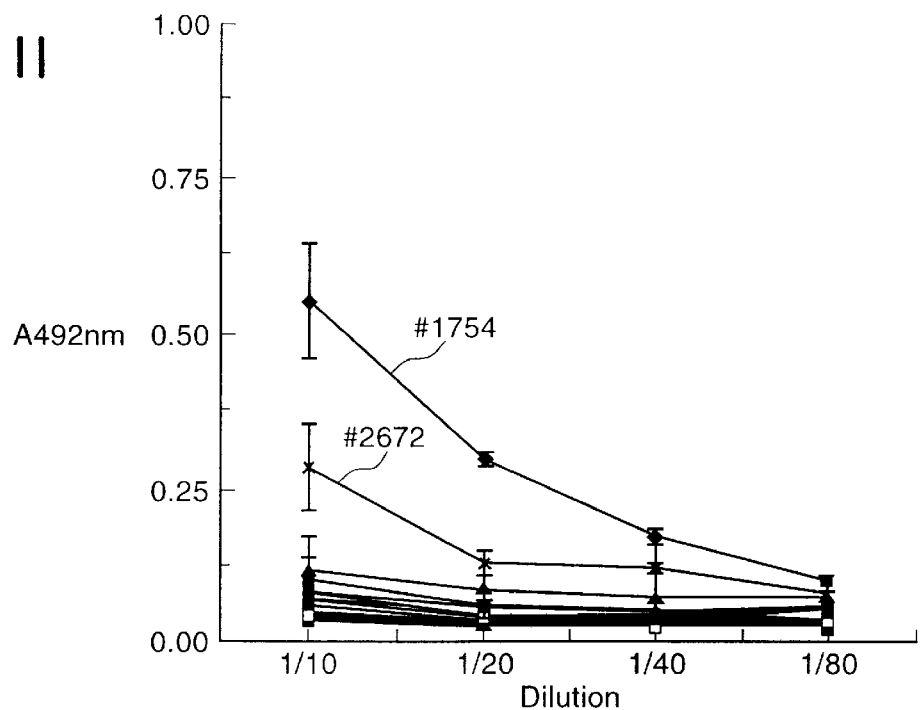
FIG. 11 This figure demonstrates that at least 10% of breast cancer patients have the antibody against mucin. Serum from breast cancer patients was reacted with the 105 amino acid synthetic peptide, and specific reactivity detected by ELISA assay. Normal serum did not react with the peptide and was used as a control. The same results were obtained with sera from pancreatice and colon cancer patients.
Figure 12:
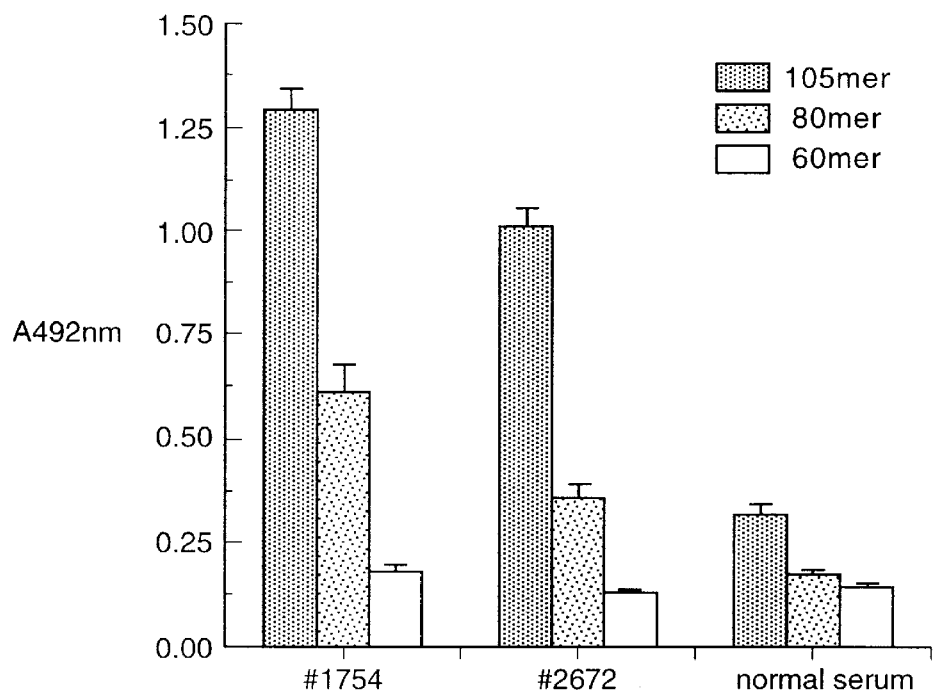
FIG. 12 This figure shows that the antibody against mucin is only detectable with the peptides of the invention, where the 105 amino acid peptide demonstrates the best results. Previous experiments performed by the inventors and others by reacting patient sera with short mucin peptides or purified mucin molecules from sera of cancer patients, detected no specific antibody.
Figure 13:
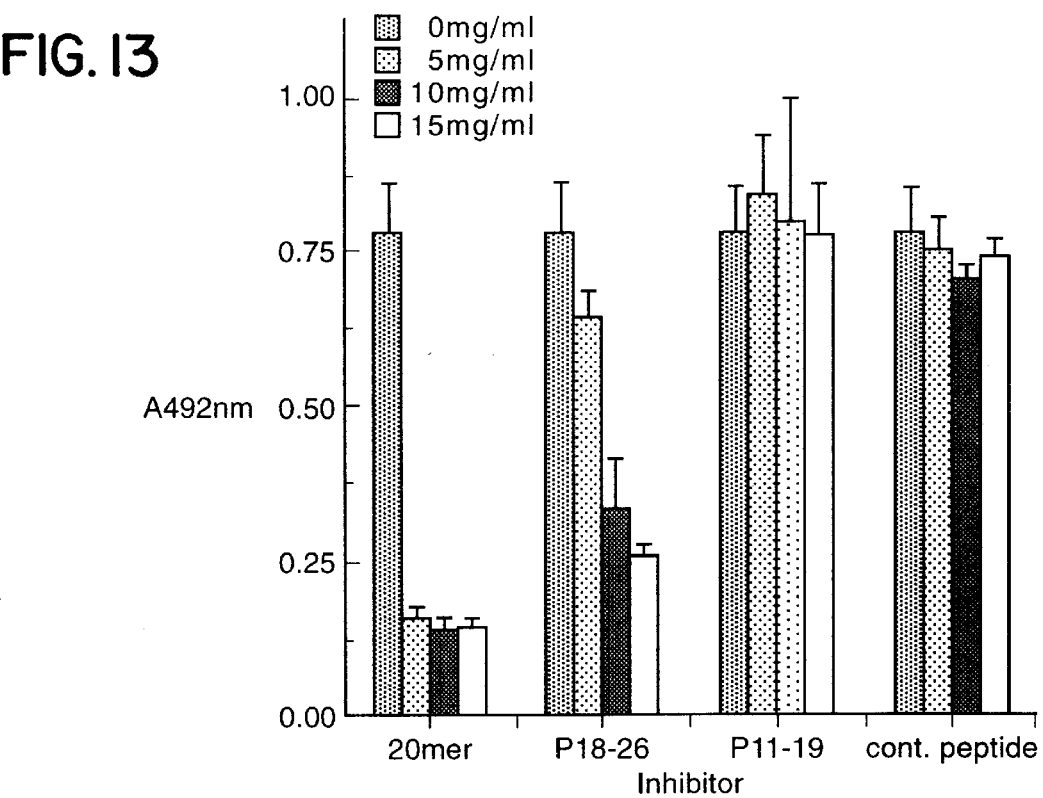
FIG. 13 This figure shows that the 105 amino acid peptide of the invention is useful in determining precisely the specificity of serum antibodies. Short peptides are used to inhibit serum reactivity with the 105 peptide. Serum is mixed first with short mucin peptides representing difference regions of the tandem repeat. The mixture is then reacted on an ELISA plate with the long 105 amino acid peptide. Short peptides with epitopes recognized by antibodies in patient's sera can interfere with the antibody binding to the long peptide.
Figure 14:
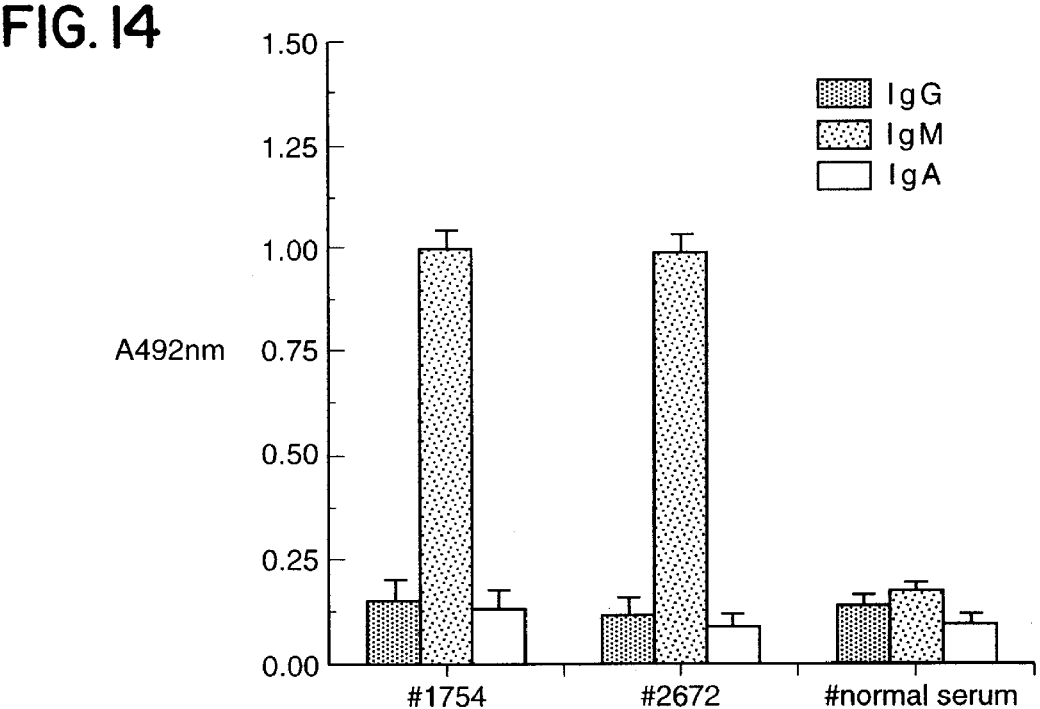
FIG. 14 This figure shows that the 105 amino acid peptide of the invention is useful in determining the precise isotype of the anti-mucin antibody. The long peptide binds the specific antibody from the patient's sera. Other antibodies are recovered by washing the ELISA plate. Secondary antibodies which are commercially available are then added. They have specific reactivities with various antibody isotypes. The end result is that antibodies from sera which bound to the 105 amino acid peptide can be determined to be either IgG, IgM, IgD, IgA or IgE, or mixtures of these. The figure shows that antibodies generated by the patients against mucin are all IgM.

FIG. 10 shows a plot of the molar ellipticity [$\theta$] at 25° C. for the mucin 20, 60 and 105 amino acid peptides, PRN60, H2Dmuc7 and a ten amino acid control peptide (TAENAEYLRV) (see SEQ ID NO:30) that does not contain proline. Clearly, the proline rich peptides exhibit dramatically greater [$\theta$] indicating the formation of secondary structure (FIG. 10). The ratio of [$\theta$] of the proline rich peptides to [$\theta$] of the control peptide at 25° C. ranges from 3.2 for the mucin 20 amino acid peptide to 21.1 for the mucin 105 amino acid peptide. These enhanced [$\theta$] with increasing numbers of mucin tandem repeats correlates with the formation of native secondary structure as detected by $^1$H-NMR spectroscopy and monoclonal antibody binding data (Fontenot et al., in press 1993A).

EXAMPLE 2

Monoclonal antibodies to native muc-1 recognized the synthetic peptides.

Monoclonal antibodies may be obtained by methods well known in the art. For instance, antibodies may be obtained by immunizing mice with human tumor cells which express mucin, or with purified human mucin which was or was not stripped of sugars. Monoclonal antibodies were produced by standard Kohler Milstein hybridoma technology.

To verify that synthetic peptides corresponding to one-, two-, and three-tandem repeats of muc-1 protein core fold into the native structure, the peptides were reacted with a panel of muc-1 specific monoclonal antibodies (Table 2). These antibodies were previously shown to react with epitopes specific for the carcinoma associated form of muc-1 (Taylor-Papadimitriou, Int. J. Cancer, 49:1–5, 1991 and Jerome, et al., Cancer Res., 52:5985–5990, 1992). The antibodies were reacted against equal quantities of the synthetic peptides in a solid-phase ELISA. The reactivity is defined as the slope of the color change with time.

Most antibodies failed to react with a twenty amino acid peptide corresponding to one repeat and beginning with proline 1 (Table 2). However, these antibodies reacted with peptides corresponding to two- and three-tandem repeats of the protein core. A probable explanation for this is that native presentation of the predominant epitope (PDTRP) recognized by these antibodies requires at least the alanine of the previous repeat. This observation could explain the results obtained by others showing that other amino acids can be substituted for alanine, and that peptides linked to a carrier or a pin will react without alanine (Price, et al., Molecular Immunology, 27:795–802, 1990 and Xing, et al., Immunology, 72, 1991). The increase in reactivity of the monoclonal antibodies with the 40 and 60 amino acid peptides indicates that the epitopes attain a native conformation in the absence of glycosylation, reflecting the structure seen in native mucin.

EXAMPLE 3

Mucin protein core formed a stable folded secondary structure.

Figure 1A:
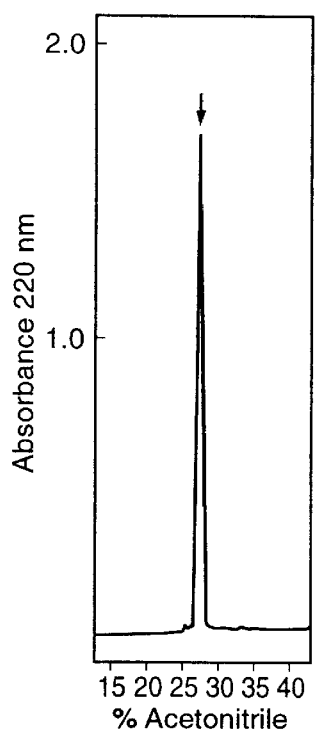
FIG. 1 The analytical HPLC chromatograms of the crude synthetic peptide products of the twenty, forty, and sixty amino acid peptides are shown above. The electrospray mass spectra of the largest HPLC peak fractions (indicated by arrow) are shown below. In each case the mass obtained was the expected molecular weight (20 mer=1886 daltons, 40 mer=3766 daltons, 60 mer=5625 daltons).
Figure 1B:
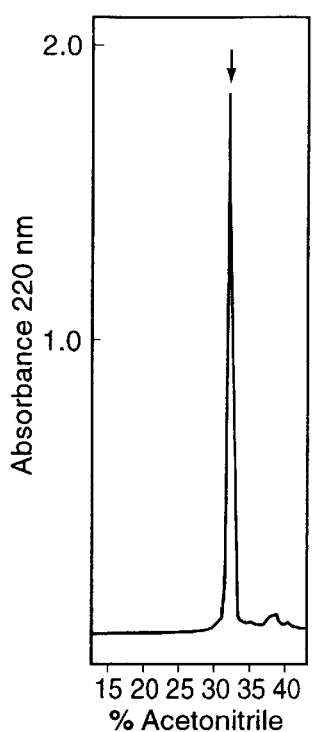
Figure 1C:
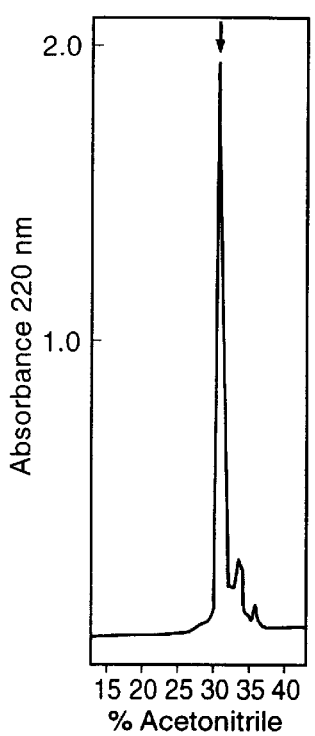
Figure 1D:
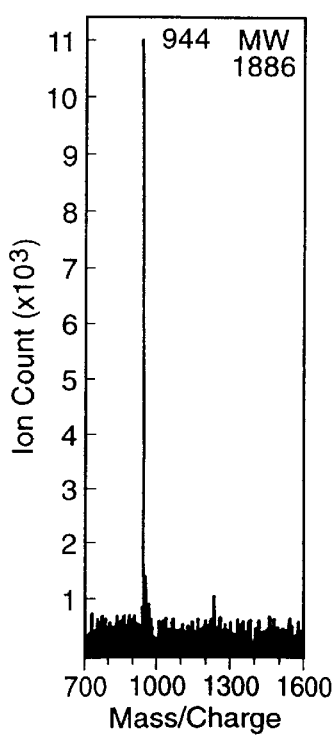
Figure 1E:
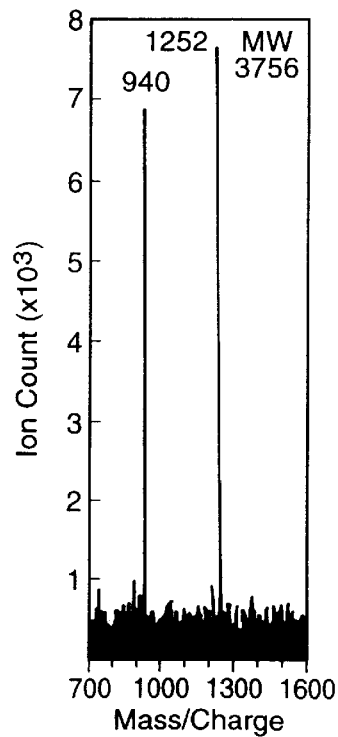
Figure 1F:
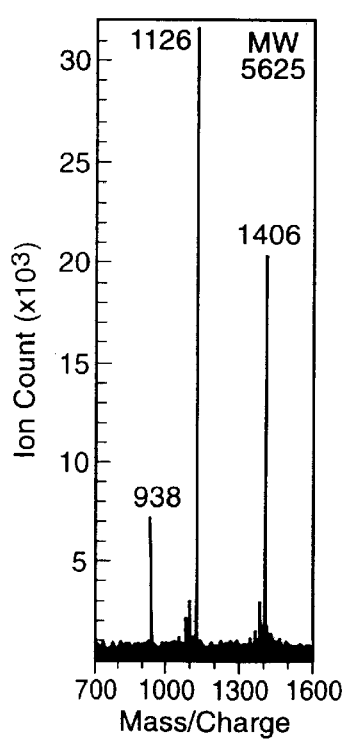
Figure 2:
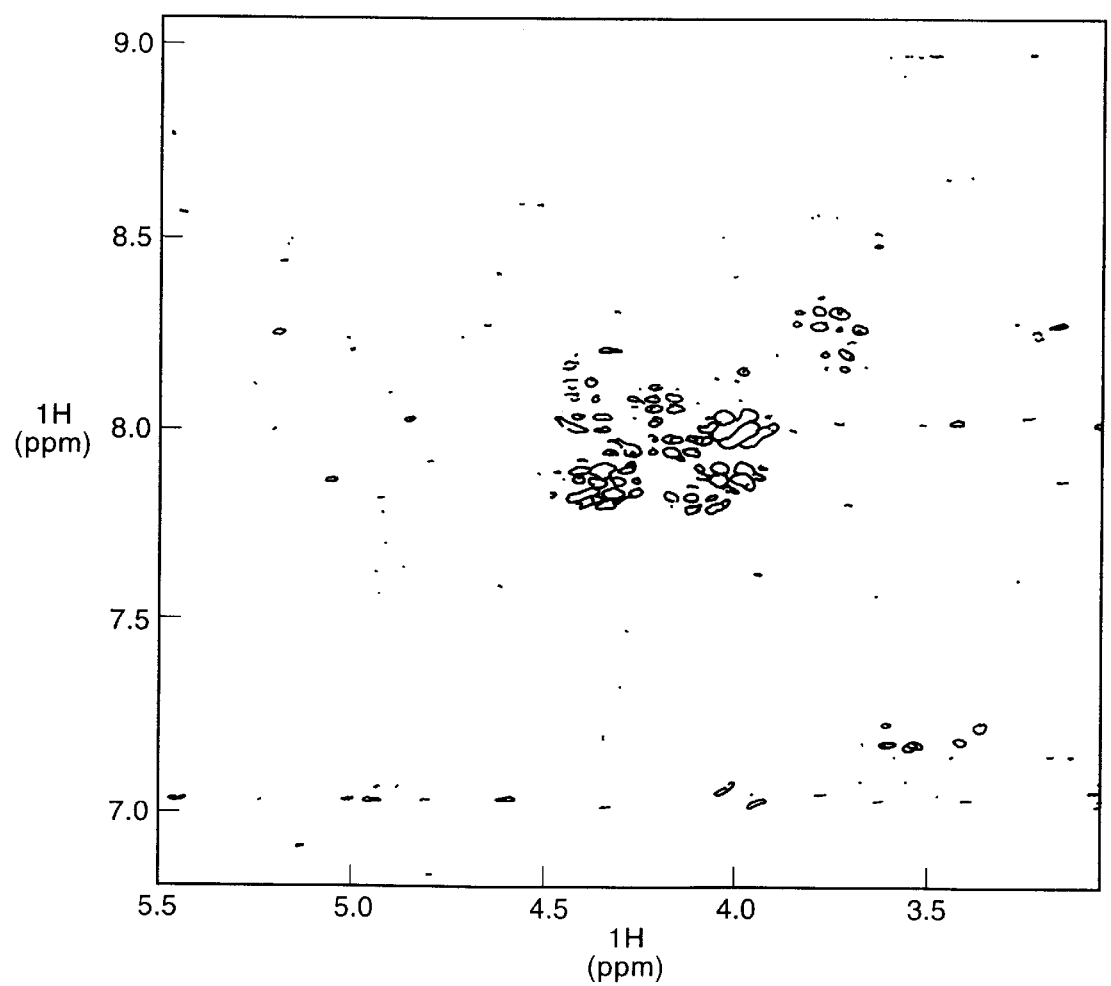

A finger print region of the two-dimensional correlated spectroscopy (COSY) of the mucin 60 amino acid peptide in D$_2$O (FIG. 2) clearly shows cross peaks of some nonexchangeable amide protons. This particular region of the spectrum shows scalar correlation between amide-$^1$H and $^1$H-alpha protons. These cross peaks did not exchange during the duration of more than 12 hours at 27° C. Thus, these amide protons appear to be protected very well inside the 3-dimensional structure of the folded mucin. This experiment clearly shows that a mucin 60 amino acid peptide retains a stable ordered structure in solution, in distinct contrast to the random coil conformation previously reported (Jentoft, Trends Biochem. Sci., 15: 291–294, 1990).

EXAMPLE 4

Development of structure requires multiple tandem repeats.

FIG. 3 shows the region of the $^1$H-NMR spectrum which is characteristic of β-protons of the amino acid side chains. The muc-1 tandem repeat sequence contains only one aspartic acid (D) and one histidine (H) residue per TR, and the side chain, β-protons of these an amino acids are resolved into two distinct regions of the spectrum (Wuthrich, NMR of proteins and mucleic acids, John Wiley and Sons, New York, N.Y., 1986). FIG. 3 shows the spectrum of the free amino acids as compared to the spectrum of the synthetic peptide corresponding to one-tandem repeat, two-tandem repeat, and three-tandem repeat peptides. Arrows indicate differences in the spectra associated with increasing numbers of tandem repeats in the peptide. These spectra indicate that the development of an ordered structure depends on the number of tandem repeats (size) in the peptide. If the secondary structure of these peptides were random coil, the spectrum in this region would be expected to be independent of the number of repeats present and to correspond closely to that of the free amino acids (Wuthrich, NMR of proteins and mucleic acids, John Wiley and Sons, New York, N.Y., 1986). The data in FIG. 3 show clearly that the spectrum is dependent on the number of repeats and is significantly different from the spectra observed for free amino acids.

Free amino acids, or peptides containing one, two or three 20 amino acid repeats of muc-1 core all contain the same information when considering the $^1$HNMR responsive protons in the region of the spectrum from 1.6 to 3.3 ppm from DSS (Wuthrich, NMR of proteins and mucleic acids, John Wiley and Sons, New York, N.Y.,). Differing chemical shifts and numbers of peaks are the result of changes in the local magnetic fields arising from structural changes (folding) of the peptide backbone. Of particular interest in FIG. 3 are the distinct spectral changes occurring in the aspartic acid, β-proton resonances (2.4 to 2.7 ppm) when going from free amino acids to one-, two-, and three-tandem repeats. Similarly, structural changes are evident from the changes in the histidine β-proton resonances (2.9 to 3.3 ppm) as the number of protein tandem repeats increases. These results can be interpreted to indicate that an ordered structure is not completely formed in a peptide with only one 20 amino acid repeat, and that the larger peptides containing 2 and 3 tandem repeats contains sufficient folding information to result in a cooperative formation structure.

EXAMPLE 5

Intrinsic viscosity measurements support a folded rod-shaped structure.

The intrinsic viscosity [η] ml/g is a sensitive measure of the state of folding, and the molecular shape (globular vs. rod-like) of a protein (Tanford, Physical Chemistry of Macromolecules, John Wiley and Sons, New York, N.Y., pp. 798–799, 1961 and Tanford, et al., 1967). Tanford has shown that for a protein in a random coil state, the intrinsic viscosity [η] ml/g is at a maximum and is given by the equation [η] ml/g=0.684 n$^{0.67}$ where n is the number of amino acids in the protein. The random coil intrinsic viscosity of a protein depends only on the number of residues. For a 60 amino acid peptide the intrinsic viscosity value is predicted to be 10.7 ml/g. The measured value for the muc-1 synthetic peptide with 3 repeats is 7.71 ml/g (Table 3). This value of 7.71 ml/g would correspond to the expected intrinsic viscosity of a random coil 36 amino acid peptide. The measured value of intrinsic viscosity for the muc-1 peptide with 3 repeats is significantly less than expected if the peptide were random coil. Therefore, based on intrinsic viscosity, this peptide assumes an ordered conformation in solution, in agreement with the structure suggested by previous NMR experiments.

Intrinsic viscosity can also yield information about molecular shape. The intrinsic viscosity for all globular proteins is 3.3 to 3.9 ml/g and is independent of molecular weight (Tanford, Physical Chemistry of Macromolecules, John Wiley and Sons, New York, N.Y., pp. 798–799, 1961). The value of 7.71 ml/g for the muc-1 peptide with 3 repeats rules out a globular shape and is consistent with a rod-like shape with an axial ratio (length/width) of 9.2 (Cantor, et al., Biophysical Chemistry Part 2: Techniques for the Study of Biological Structure and Functions, W. H. Freeman and Co., New York, N.Y., 1980). This measured axial ratio value (9.2) is in agreement with the value of 9.7 determined from the molecular graphics program SYBYL in which the peptide sequence was modeled as series of type I reverse turns (Table 3).

It can be concluded from the intrinsic viscosity value that the peptide with 3 repeats forms an ordered conformation in solution that is rod-like in shape with a longitudinal span of 33–34 Å/repeat. This result suggests that the unglycosylated protein core could determine the extended structure seen in electron micrographs (Lan, et al., J. Biol. Chem., 262: 12863–12870, 1987). These results also support the hypothesis that the muc-1 protein core exists as a poly-proline β-turn helix.

EXAMPLE 6

Model of a poly-proline β-turn helix for muc-1 TR domain.

Figure 7:
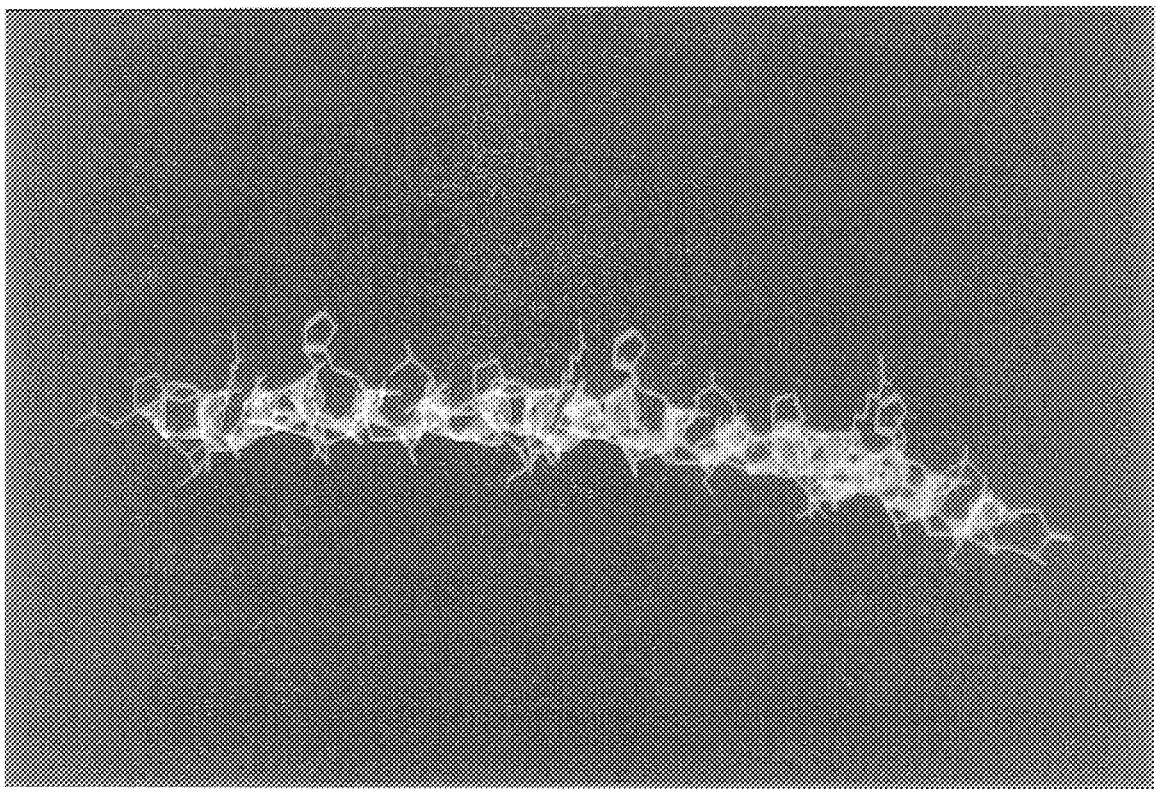
FIG. 7 The sequence of three-tandem repeats of the human mucin muc-1 gene modeled into a poly-type I turn conformation using the Tripos molecular graphics program SYBYL.

FIG. 7 shows a computer model of the sixty amino acid peptide in the poly-proline β-turn helix conformation that was created by assuming that the mucin sequence exists in a poly-type I turn conformation. This model reveals that the amino acid side chains radiate outward from an extended rod-like backbone, and are completely exposed to the solvent (FIG. 7). This orientation of the side chains facilitates accessibility of potential glycosylation sites to the glycosylation machinery. The secondary structure is not necessarily dependent on glycosylation, nor does it have to be disrupted by the addition of carbohydrate. This model explains the lack of effect that heating the peptides has on the NMR spectrum. Since no unfolding can occur in the globular sense with side chains moving from a buried hydrophobic core to an aqueous exterior, there are no large chemical shifts of the side-chain protons upon heating (Price, et al., Molecular Immunology, 27: 795–802, 1990). The model also explains why the A and DT residues will permit substitution within the primary epitope of APDTRP. When the turn is formed, the P and R amino acid side chains are in the same space and accessible for binding to the antibody. Substitutions that allow the turn to form will be tolerated.

EXAMPLE 7

Clinical trials.

Ethical Considerations

Since no "vaccination" was to be performed in patients without metastatic disease but rather a simple detection of DTH to carrier free, adjuvant free mucin peptides, it was anticipated that no or little toxicity will be incurred. Although no direct patient benefit may be accrued in these patients, such studies serve as the basis for immunotherapies which could benefit these or subsequent patients. Thirty patients (Group 3) with untreatable pancreatic, colon or breast carcinoma will receive a vaccine utilizing these peptides and adjuvant.

Schema

Patients stratified by group: (Pancreatic (P) Breast Cancer (B), colon cancer (C)

Group 1. Untreated patients (10P, 10B, 10C)

Group 2. Post-treatment group (10P, 10B, 10C)

Group 3. Advanced, metastatic group (60 pts: stratified as eligible patients present for treatment)

PBL harvest for test of T cell reactivity to mucin; and HLA typing

Immunohistochemistry of primary tumor for presence of antibody defined immunoractive mucin.

Serum tested for presence of circulating mucin or antibody to it (ELISA)

Three separate formulations were used to test immune reactivity. The first encompassed eight separate nonameric sequences consisting of the amino acids 1–9, 2–10, 3–11, 15–23, 16–24, 18–26, 20–28, and constituted peptides containing at least three of the five amino acids felt to be the likely immunogenic epitope based on prior serologic and cellular reactivity. The second preparation encompassed the other seven nonameric sequences. The third preparation consisted of a synthetic 105 amino acid polypeptide spanning 6 conserved tandem repeat observed in the mucin molecule.

Graded (1,10,100, ug) skin test to individual nine amino acid peptide pools (Preparation 1; PDTRP predominant, Preparation 2-other peptides (6–14, 7–15, 8–16, 9–17, 10–18, 11–19, 12–20, 14–22) and Preparation 3: 105 amino acid polypeptide (1–105).

Concurrent multitest (Merieux) for reactivity to common recall antigens.

Measure skin test for erythema and induration at 24 and 48 hours.

Skin punch biopsy of highest antigen dose sites: 1) immunopathology, 2) in situ cytokine gene expression 3) T cell culture 4) PCR for cytokines and Va and VS usage.

Repeat DTH testing at 3–8 weeks with two peptides with highest in vitro reactivity and a peptide with no in vitro reactivity, controlled with response to the 105 aa peptide in reactive patients. Some patients may have each of the eight peptides in a group tested individually if no in vitro tests are suggestive of peptide predominant reactivity.

Daily vital signs, amylase, lipase, BUN/Creatinine during DTH testing (0,24, and 48 hours) and at 1–4 weeks post testing.

Vaccination of group 3 patients at week 3, 6, and 9 with 100 ug of the long peptide and BCG ($5 \times 10^7$ TICE BCG, Organon Teknika Corp.; Chicago, Ill.); repeated DTH testing on three different peptide preparations at 12 weeks and assessed extent of disease.

Patient Selection

For the purposes of this evaluation patients were identified within the clinics and hospitals of the University of Pittsburgh Medical Center, primarily within facilities of the Pittsburgh Cancer Institute. Patients were either counseled by the examining and participating physician following discussion with the principal investigators or alternatively by referring the patient for initial "screening" by the protocol nurse. Following evaluation and meeting the criteria noted below, patients had the DTH tests applied and read in a blinded fashion. All patients, clinical results, X-rays, and immunologic assays were presented in an ongoing fashion at meetings held every weekly in the PCI outpatient clinic.

Eligibility Criteria

For DTH testing, patients must have had pancreatic, breast or colon carcinoma histologically proven. For immunization (Group C) patients must have had metastatic unresectable or locally recurrent disease for which no other conventional form of therapy offers a significant hope of cure or palliation.

Biopsy proven pancreatic, colonic or breast carcinoma.

Patients may have received chemotherapy prior to DTH testing. At least four weeks must have elapsed since chemotherapy.

Patients may have received prior radiotherapy provided that at least four weeks have elapsed.

A performance status of 0–2 (Zubrod) with life expectancy of at least three months.

Patients were at least 18 years of age.

Patients had at the start of treatment: WBC greater than 3,500 mm3, platelet count greater than 100,000 mm3, serum creatinine less than 1.5 mg/dl or a creatinine clearance greater than 60 cc/min., serum bilirubin less than 1.5 mg/dl.

Patients must have recovered from the effects of major surgery and must be free of infection.

Written informed consent must have been obtained.

Ineligibility Criteria:

Patients currently treated with anti-inflammatory agents including glucocorticoid therapy or NSAIDs were ineligible.

Patients without frozen or paraffin-fixed tissue available for antibody staining for mucin were ineligible.

Clinical Location:

All patients were treated at the Pittsburgh Cancer Institute's outpatient unit or alternatively in the Clinical Research Center out-patient unit. Some tests may have been administered while the patient is hospitalized at Montefiore or Presbyterian University Hospital as part of a diagnostic work-up.

Duration of study:

12 months.

Assessment plan:

DTH Testing

Three separate formulations were used to test immune reactivity. The first encompassed eight separate nonameric sequences consisting of the amino acids 1–9, 2–10, 3–11, 15–23, 16–24, 18–26, 20–28, and constituted peptides containing at least three out of the five amino acids felt to be the likely immunogenic epitope based on prior serologic and cellular reactivity. The second preparation encompassed the other seven nonameric sequences. The third preparation consisted of a synthetic 105 amino acid polypeptide spanning 5 perfectly conserved tandem repeat observed in the mucin molecule.

Dose:

Each DTH consisted of up to three separate injections of 0.05 ml/site injected intradermally and consisted of 1 mcg, 10 mcg, or 100 mcg of each preparation. Equimolar concentrations of each of the constituent nonameric sequences were prepared randomly as determined by a statistician, and placed in syringes numbered one through nine. All testing was performed on the posterior trunk at 2, 4, and 6 cm from the midline and each set of three tests (total of nine) separated by at least 2 cm in the vertical axis. On the contralateral part of the posterior trunk the multitest CMI skin test with antigens for cellular hypersensitivity (Merieux) was applied. Each test contained a disposable plastic applicator which was pre-loaded with seven delayed hypersensitivity skin test antigens and a glycerine negative control for percutaneous administration: tetanus toxoid antigen, diphtheria toxoid antigen, streptococcus antigen, old tuberculin, candida antigen, trichophyton antigen, and proteus antigen (NDC 50361-780-80).

Schedule:

DTH for both the standard recall antigens as well as mucin derived peptides was performed on day 0 and measured at 24, 48, and 72 hours. Skin tests were read and perpendicular diameters for erythema and induration were recorded for each skin test.

Serum for assay of circulating mucin and detection of antibodies to mucin:

Two red-topped tubes of whole blood were drawn prior to DTH testing.

Sixty ml of heparinized whole blood (six green-topped tubes) for in vitro T-cell reactivity to individual mucin peptides were obtained immediately prior to DTH testing.

Six mm punch biopsies were obtained under local anesthesia for positive skin tests to the mucin peptides and as a control to any of the positive recall antigens. If no reactivity was observed, a biopsy of each of the highest concentrations (100 ug) applied was biopsied. One half of the punch biopsy was embedded in OCT for in situ cytokine assays and immunohistochemistry. One half was delivered to Dr. Finn's laboratory for expansion of T-cells.

Serum amylase, lipase, and creatinine were obtained prior to immunization and at 24, 48 and 72 hours following immunization.

Follow-up:

Patients were observed at one week and at three weeks for evidence of untoward responses as part of the routine follow-up of the patient for their underlying disease.

Vaccine protocol:

Patients in Groups 3, regardless of the skin test result subsequently underwent vaccination at a separate site with 100 g of p105 peptide and 5×107 lyphoilized TICE BCG colony forming units (Organon Teknika Corp, Chicago, Ill.) in )0.15 ml of saline for injection, USP.

Schedule:

Patients were administered the vaccine at three weeks, six weeks, and nine weeks following the initial DTH testing and re-tested with peptide as noted above for DTH at 8 weeks. Patients were also re-assessed at 8 weeks for evidence of anti-tumor responses using conventional radiographic criteria.

Patients underwent serum studies for amylase, lipase, and creatinine at three weeks, six weeks, and 12 weeks.

Evaluation and management of toxicity:

All toxicity was to be graded using the common toxicity criteria. Previously unknown or severe toxicity was to be reported to the NCI as adverse drug reactions.

NCI requirements for Phase I ADR reporting were followed. It was the responsibility of the principal investigator to report by telephone to the IDB (301-496-7957, available 24 hours) within 24 hours of any of the following events: all life-threatening events (Grade 4) which may be due to drug administration; all fatal events; and all first occurrences of any previously undefined toxicity regardless of grade. Written report was to follow within 10 days to the Investigational Drug Branch, P.O. Box 30012, Bethesda, Md. 20814.

Dose modification:

There was no dose modification in this protocol.

Diagnostic studies and therapy plan:

All pilot patients eligible for this skin test protocol following appropriate informed consent underwent the DTH testing as noted above. Subsequent therapies may have been administered as early as 24 hours following the completion of the skin test reading.

Therapy modification:

Pathological changes/tumor host factors: Patients with evidence of an untoward responses including allergic or atopic responses were to be treated as appropriate symptomatically. Patients with vigorous systemic response including anaphylaxis were not to be further skin tested or subjected to vaccination.

Study parameters to be measured (i.e. serial observations):

Pre-study tests.

CBC with differential, LFTs, creatinine, BUN, amylase, and lipase.

Interim exams and frequency of evaluation:

As noted above amylase, lipase, and creatinine, as well as physical examination were performed on patients undergoing this study at the conclusion of 72 hours of observation for skin test reactivity.

Patients were considered off study in Group 1 or Group 2 one week after evaluation of DTH reactivity, except for follow-up regarding death or time to disease progression.

Evaluation criteria:

The major endpoints of this study were the in vivo and in vitro assays of immunity against mucin peptides. The inventors also evaluated the effect of vaccine treatment on immunity against autologous breast, colon or pancreatic cancer and the correlation of immune responses in each category to disease response and/or disease progression.

The immunologic endpoints in order of priority were: DTH against peptide skin tests; cellular cytotoxicity and proliferation against individual peptides from biopsy sites or peripheral blood; and humoral response to recombinant mucin or evidence of circulating mucin.

The clinical parameters that were followed included: objective evidence of tumor regression; progression for each survival; overall survival (to be compared in each of the different groups 1, 2, and 3). (The definition of these parameters in the clinical test were formed for evaluation of disease progression as described below.)

Complete Response:

Complete disappearance of all measurable lesions with no new lesions developing and maintained for greater than four weeks. Complete response was dated from the time all lesions disappear.

Partial response:

At least a 50% reduction in the size of all measurable tumor areas as measured by the product of the greatest length and the maximum width.

No change:

A decrease of less than 50% or an increase of less than 25% of the sum of the products of the perpendicular diameters of all measurable lesions.

Progression:

A 25% greater increase of original measurements in the sum of the products of the perpendicular diameters of measurable lesions and/or occurrence of new lesions. If possible, any new lesions were to be biopsied to confirm progression.

| Study parameters: | | | | | | |
|---|---|---|---|---|---|---|
| | Prior to therapy | Day 0 | Day 1 | Day 2 | Day 3 | Week 1–4 |
| History and Physical Exam | X | X | | | | X |
| Weight | | X | X | | | X |
| Tumor Measurements | | X | X | | | X |
| Performance Status | X | X | | | | X |
| CBC, platelets, differential | | X | X | | | X |
| Chemistry Profile, Amylase, lipase | | X | X | X | | X |
| PT/PTT | | X | X | | | X |
| Chest x-ray | | X | X | | | X |
| EKG | | X | X | | | X |
| Special x-rays as needed for tumor measurement | | X | X | | | X |
| Measurement skin test | | | X | X | X | |
| Punch biopsy for molecular immune testing | | | X | X | | |

Registration:

Patients were registered on study by the protocol nurse and/or the senior investigator by completion of a study form, obtaining of informed consent, and application of the first skin test.

Statistical considerations:

The primary endpoint of the study was the determination of DTH reactivity to individual peptides. Statistical analysis involved evaluation of the degree of DTH and/or evidence of response to the vaccine in Group 3.

Goals of the Analysis

The primary objectives of the statistical analysis were to:

(1) quantify and summarize the delayed type hypersensitivity (DTH) response to three different preparations of mucin peptides, presented at each of three concentrations to patients with breast, colon or pancreatic cancer;

(2) determine whether the preparations differ in terms of the strength of the responses they elicit;

(3) determine whether there is an increasing dose-response relationship over the range of concentrations tested;

(4) investigate possible differences in response patterns between disease groups;

(5) determine whether responses differ between treatment naive patients, patients having completed treatment who are without apparent disease, and patients with metastatic or untreatable cancer;

(6) correlate DTH responsiveness with the degree of infiltration of T-cell subpopulations found adjacent to the location of injection, and to circulating mucin levels;

(7) investigate the association between DTH responsiveness to much peptides and patients' general anergic/nonanergic status as measured by a concurrently administered panel of standard recall antigens.

A secondary phase of the analysis considered those patients with metastatic or untreatable disease, who following DTH testing are to receive three immunizations at three-week intervals. Here, the principal questions of interest are:

(1) Does DTH testing subsequent to immunization indicate an increased level of responsiveness relative to pre-immunization baselines?

(2) Are there pre-post changes in patterns of T-cell infiltration at the injection site, or in circulating mucin levels?

(3) Are there indications of association between clinical response and baseline DTH responsiveness?

Study Design

Patients participating in the study were drawn from the six groups shown in FIG. B.2:

| FIG. B.2: Study Groups | | | |
|---|---|---|---|
| | Pre-Treatment | Post-Treatment Disease-Free | Untreatable/ Metastatic |
| Breast CA | N = 10 | N = 10 | N = app. 20 |
| Pancreatic CA | N = 10 | N = 10 | N = app. 20 |
| Colon CA | N = 10 | N = 10 | N = app. 20 |

There were 30 patients entered in each of the first two treatment groups, and 60 patients entered in the third group, for a total of 120 patients on this protocol. Each patient was then DTH tested against all nine combinations of three mucin peptide preparations (A,B,C) and concentrations (1 mcg, 10 mcg, 100 mcg).

Specific descriptions of the peptide preparations are reported above. Each of the nine tests was administered by intradermal injection of 0.05ml, with the order and relative placement of the injections randomized for each patient to avoid interactive biases that could otherwise conceivably occur. The syringes used for injection were preloaded and blinded in such a way that neither the patients, the personnel performing the injections, nor those responsible for measurement of induration had knowledge of the placement of the tests.

The structure of the study design was therefore factorial, with two between-patient factors (Disease and Treatment Status) and two within-patient factors (Peptide Preparation and Concentration). DTH response was assessed at 24 and 48 h following injection (so that time could be considered a third within-subject factor). Strength of the response was quantified by determining the product of the largest diameter of the induration and its perpendicular (proportional to the area of induration) at each time point. For purposes of analysis the maximal area of induration over the 72 h observation period served as the primary endpoint of interest.

Analysis Methods:

Analysis of DTH Response: The statistical methods which was most appropriate for analysis depended strongly on the nature of the DTH responses observed over the course of the study. If the large majority of patients measurably responded to each of the peptide preparations, then the treatment of the area of induration as an interval-scaled variable would be indicated. In this case, the goals of the analysis specified above may be addressed by use of repeated measures analysis of variance methods described in the following references: Winer, B J, Statistical Principles in Experimental Design, 1971, McGraw-Hill, New York, N.Y.; Crowder, MJ and Hand, DJ Analysis of Repeated Measures, 1990, Chapman and Hall, London; Milliken, George A., and Johnson, Dallas E., Analysis of Messy Data, Vol. 1: Designed Experiments, 1984, Wadsworth, Belmont Calif.

On the other hand, if positive DTH responses are noted in only a fraction of patients, with a significant proportion of nonresponders, the usual methods of repeated measures analysis would not be appropriate. Instead, the approach taken would involve the classification of responses into ordered categories. Depending on the nature of the data at hand, the best method of categorization may vary from a simple "No Response"/"Response" dichotimization to a more complicated set of ordered categories, e.g. "No Response", "Response only at 100 mcg", "Response only at >=10 mcg", "Response at >=1 mcg". Methods of repeated measures analysis appropriate to categorical responses are described in Prowder, MJ and Hand, DJ Analysis of Repeated Measures, 1990, Chapman and Hall, London, and in Agresti, Alan, Categorical Data Analysis, 1990, John Wiley & Sons, New York, N.Y. For example, a formal test of equivalence of response profiles across the three peptides may be carried out by use of the CMH ANOVA statistic applied to patient-stratified peptide by-response contingency tables.

It is not unlikely that the peptide formulation consisting of the amino acids 1–9, 2–10,3–11,15–23,16–24, 18–26 and 20–28 would typically result in measurable responses suitable for analysis on an interval scale, while the remaining preparations would produce few responses. In such a case, following initial analyses of an ordinal nature formally comparing the three preparations, subsequent and more detailed analysis of the first preparation would be carried out by means of classic repeated measures methods.

Analysis of Vaccination Effects: In this phase of the investigation, postvaccination DTH responses were to be compared with baseline responses in the 10 metastatic breast cancer patients and the 10 metastatic pancreatic cancer patients, in order to determine whether vaccination is effective in enhancing DTH responsiveness. Formal statistical tests of effect were to be carried out by classic or categorical repeated measures analysis, as appropriate. Tests for the occurrence of post-vaccination changes in T-cell infiltrate levels and circulating mucin levels were similarly conducted.

It was also of interest to investigate the possible association of clinical responses with pre-vaccination parameters, and in particular with baseline DTH response. This was done by means of logistic regression modeling. Due to the limited sample size involved in this phase of the investigation, and because the frequency of clinical response cannot be expected to be large, p-values were generated by means of exact permutation tests. For these same reasons, it was unlikely that statistically significant association would be detected here, even if in fact the true correlation between clinical response and prior DTH response is large.

Time frame:

A total of 120 patients entered into this study. This required over a one year time period that one to two patients be entered per week. Two to four patients with pancreatic cancer were seen each week and well over 10–20 patients with breast cancer. It was anticipated that this protocol may be completed within six months and that other questions may need to be addressed.

The entire contents of all references cited herein above are hereby incorporated by reference.

While the foregoing invention has been described in some detail for purposes of clarity and understanding, it will be clear to one skilled in the art from a reading of this disclosure that various changes in form and detail can be made without departing from the true scope of the invention.

TABLE 1

Sequences Analysis of Human Mucin Tandem Repeats

| Mucin Gene | Muc-1 | Muc-2 | Muc-3 | Muc-4 |
|---|---|---|---|---|
| # Amino Acids/repeat | 20 | 24 | 17 | 16 |
| % Proline | 25 | 21 | 6 | 6 |
| % Threonine | 15 | 62 | 41 | 25 |
| % Glycine | 20 | 4 | 0 | 0 |
| % Ser + Thr | 25 | 62 | 70 | 50 |
| # Turns/Repeat[a] | 3 | 2 | 1 | 1 |

[a]: Predicted by Chou and Fasman rules

TABLE 2

Monoclonal Antibody Recognition of Mucin Peptides

| | | Reactivity in ELISA | | |
|---|---|---|---|---|
| Antibody | Epitope | 20 mer | 40 mer | 60 mer |
| HMFG2 | DTR | 4.5 | 17 | 17 |
| 139H2 | CORE | 2.2 | 30 | 34 |
| 175C5 | ? | 2.3 | 15 | 36 |
| 201E9 | ? | 29.0 | 100 | 121 |
| BC1 | (A) PDTR (see SEQ ID NO: 31) | 7.0 | 27 | 14 |
| BC2 | (A) PDTR (see SEQ ID NO: 31) | 2.7 | 17 | 18 |
| BC3 | (A) PDTR (see SEQ ID NO: 31) | 4.8 | 100 | 83 |

TABLE 3

Molecular Dimensions of Mucin 60 Amino Acid Peptide

| | |
|---|---|
| Intrinsic Viscosity [η] ml/g | 7.7 |
| Axial Ratio (a/b) from [η] ml/g | 9.2 |
| Axial Ratio (a/b) from Molecular Graphics | 9.7 |
| Length (A) per TR from Molecular Graphics | 35 |

TABLE 4

Sequences of Proline Rich Peptides

| No. | Gene | Repeat Sequence (see SEQ ID NOS: 30–36, respectively) | Copies |
|---|---|---|---|
| 1. | mucin | PDTRPAPGSTAPPAHGVTSA | 1–5.25 |
| 2. | FeLV-PRN60 | TITPPQAMGP NLVLPDQKPP SRQSQTGSKV ATQRPQTNES APRSVAPTTV GPKRIGTGDR | 1 |
| 3. | PRN42 | TPPQAMGPNL VLPDQKPPSR QSQTGSKVAT QRPQTNESAPRS | 1 |
| 4. | H2D8 | YPHFMPTNL | 5,8 |
| 5. | H2DMUC7 | YPHAMPTNLS | 7 |

TABLE 5

Mass Analysis of Synthetic Peptides

| Gene | No. Copies | Predicted MW | Actual MW |
|---|---|---|---|
| mucin | 1 | 1887 | 1886 |
| mucin | 2 | 3756 | 3756 |

TABLE 5-continued

Mass Analysis of Synthetic Peptides

| Gene | No. Copies | Predicted MW | Actual MW |
|---|---|---|---|
| mucin | 3 | 5625 | 5625 |
| mucin | 4 | 7495 | 7492 |
| mucin | 5.25 | 9780 | 9778 |
| FeLV | 1 | 6305 | 6303 |
| PRN60 | | | |
| PRN42 | 1 | 4483 | 4482 |
| H2D8 | 5 | 5525 | 5526 |
| H2D8 | 8 | 8829 | 8834 |
| H2DMUC7 | 7 | 7805 | 7806 |

TABLE 6

ANTI-MUCIN CTLp PRE- AND POST-VACCINATION

| | CTLp | |
|---|---|---|
| PATIENT | pre- | post- |
| P-3 #2 | 1/1069035 | 1/614384 |
| C-3 #2 | 1/25419 | 1/17966 |
| B-3 #1 | 1/337287 | 1/203493 |
| P-3 #1 | 1/236981 | 1/161318 |

TABLE 7

ANTI-MUCIN ANTIBODY PRE- AND POST-VACCINATION

| | IgM | | IgG | |
|---|---|---|---|---|
| PATIENT | pre- | post- | pre- | post- |
| C-3 #10 | − | − | − | − |
| B-3 #6 | − | − | − | − |
| C-3 #9 | − | − | − | − |
| P-3 #8 | + | + | − | − |
| P-3 #7 | − | − | + | + |
| P-3 #1 | − | − | − | − |
| C-3 #7 | ++ | ++ | − | − |
| B-3 #4 | − | − | + | + |
| C-3 #2 | + | + | − | − |
| C-3 #13 | ++ | ++ | − | − |
| B-3 #1 | − | + | − | + |
| P-3 #3 | − | − | + | + |

TABLE 8

| | PRE VACCINATION DTH | | |
|---|---|---|---|
| NUMBER OF PATIENTS | 25 (colon) | 22 (pancreatic) | 8 (breast) |
| NO. of Non-Responders | 5/25 | 3/22 | 3/8 |
| NO. of Responders to all | 1/25 | 2/22 | 0/8 |
| NO. of Responders to 105mer | 16/19 | 17/17 | 4/5 |
| NO. of Responders to 9mer (+PDTRP) | 14/19 | 15/17 | 1/5 |
| No. of Responders to 9mer (−PDTRP) | 10/19 | 10/17 | 3/5 |

TABLE 9

PRE-VACCINATION DTH IN COLON CANCER PATIENTS

| PATIENT | 9mer (+PDTRP) | 9mer (−PDTRP) | 105mer |
|---|---|---|---|
| C-3 #21 | + | − | ++ |
| C-3 #22 | − | + | + |
| C-3 #23 | ++ | ++ | + |
| C-3 #24 | +++ | ++ | − |
| C-3 #10 | − | ++ | + |
| C-3 #26 | ++++ | − | ++ |
| C-3 #14 | ++ | − | + |
| C-3 #17 | ++ | − | − |
| C-3 #2 | + | − | + |
| C-3 #7 | ++ | − | + |
| C-3 #5 | ++ | + | + |
| C-3 #12 | + | − | ++ |
| C-3 #20 | + | − | + |
| C-3 #18 | − | + | ++ |
| C-3 #13 | + | ++ | − |
| C-3 #3 | ++ | − | + |
| C-3 #4 | − | + | ++ |
| C-3 #1 | − | ++ | +++ |
| C-3 #19 | + | + | ++ |
| | 14/19 | 10/19 | 16/19 |
| C-3 #8 | − | − | − |
| C-3 #25 | − | − | − |
| C-3 #9 | − | − | − |
| C-3 #6 | − | − | − |
| C-3 #16 | − | − | − |
| C-3 #11 | + | + | + |

TABLE 10

PRE-VACCINATION DTH IN PANCREATIC CANCER PATIENTS

| PATIENT | 9mer (+PDTRP) | 9mer (−PDTRP) | 105mer |
|---|---|---|---|
| P-3 #18 | + | +++ | +++ |
| P-1 #1 | ++ | −− | ++ |
| P-3 #5 | − | − | ++ |
| P-3 #19 | − | + | +++ |
| P-3 #9 | + | − | ++ |
| P-3 #12 | ++ | ++ | + |
| P-3 #3 | + | − | ++ |
| P-3 #7 | ++ | − | − |
| P-3 #8 | + | +++ | +++ |
| P-3 #15 | + | +++ | ++ |
| P-3 #14 | +++ | +++ | + |
| P-3 #1 | − | − | ++ |
| P3 #10 | + | ++ | +++ |
| P-3 #17 | ++ | + | + |
| P-2 #1 | + | − | + |
| P-3 #4 | +++ | − | − |
| | 15/17 | 10/17 | 17/17 |
| P-3 #20 | − | − | − |
| P-3 #13 | − | − | − |
| P-3 #16 | − | − | − |
| P-3 #16 | + | + | + |
| P-3 #11 | + | + | + |

TABLE 11

PRE-VACCINATION DTH IN BREAST CANCER PATIENTS

| PATIENT | 9mer (+PDTRP) | 9mer (−PDTRP) | 105mer |
|---|---|---|---|
| B-3 #2 | − | ++ | + |
| B-3 #7 | − | − | + |
| B-3 #6 | − | + | ++ |
| B-3 #1 | − | − | + |
| B-3 #8 | + | + | − |
| | 1/5 | 3/5 | 4/5 |
| B-3 #3 | − | − | − |
| B-3 #5 | − | − | − |
| B-3 #4 | − | − | − |

What is claimed is:

1. A method of detecting the presence of antibodies to pancreatic cancer, breast cancer or colon cancer in a biological test sample, comprising the steps of:

a) contacting a synthetic muc-1 peptide with a biological test sample suspected of containing antibodies to at least one of pancreatic cancer, breast cancer or colon cancer, under conditions such that a synthetic muc-1 peptide-antibody complex is formed, wherein said synthetic muc-1 peptide comprises at least two 20-amino acid tandem repeats of muc-1, and which synthetic muc-1 peptide is capable of attaining native conformation in the absence of glycosylation, and b) detecting the formation of said synthetic muc-1 peptide-antibody complex, which complex is indicative of the presence of antibodies to pancreatic cancer, breast cancer or colon cancer in said biological test sample.

2. The method according to claim 1 wherein the synthetic muc-1 peptide comprises five sequential 20-amino acid tandem repeats of muc-1 and five additional amino acids, wherein said five additional amino acids precede the first of the five sequential 20-amino acid tandem repeats or follow the fifth of the five sequential 20-amino acid tandem repeats.

3. The method according to claim 1 wherein the synthetic muc-1 peptide comprises at least three 20-amino acid tandem repeats of muc-1.

4. The method according to claim 1 wherein the synthetic muc-1 peptide comprises at least four 20-amino acid tandem repeats of muc-1.

5. The method according to claim 1 wherein the antibodies are specific to pancreatic cancer.

6. The method according to claim 1 wherein the antibodies are specific to breast cancer.

7. The method according to claim 1 wherein the antibodies are specific to colon cancer.

8. The method according to claim 2, wherein the synthetic muc-1 peptide has the composition GVTSAPDTRPAPGSTAPPAHGVTSAPDTRPAPGSTAPPAH-GVTSAPDTRPAPGSTAPPAHGVTSA PDTRPAPGSTAPPAHGVTSAPDTRPAPGSTAPPAHGVTSA.

* * * * *